(12) United States Patent
Ohyama et al.

(10) Patent No.: US 6,929,643 B2
(45) Date of Patent: Aug. 16, 2005

(54) RESECTOSCOPE APPARATUS AND ELECTRIC OPERATION APPARATUS

(75) Inventors: Masahide Ohyama, Hino (JP); Kazuya Hijii, Tama (JP); Shinji Hatta, Hachioji (JP); Kenji Harano, Hachioji (JP); Takeaki Nakamura, Hino (JP); Shuichi Kimura, Hachioji (JP)

(73) Assignee: Olympus Corporation, Tokyo (JP)

( * ) Notice: Subject to any disclaimer, the term of this patent is extended or adjusted under 35 U.S.C. 154(b) by 102 days.

(21) Appl. No.: 10/413,695

(22) Filed: Apr. 15, 2003

(65) Prior Publication Data

US 2004/0019351 A1 Jan. 29, 2004

(30) Foreign Application Priority Data

Apr. 15, 2002 (JP) ........................................ 2002-112393
Apr. 15, 2002 (JP) ........................................ 2002-112394
Apr. 15, 2002 (JP) ........................................ 2002-112398

(51) Int. Cl.$^7$ ............................................. A61B 18/18
(52) U.S. Cl. .......................... 606/46; 606/32; 606/42; 606/48; 606/50
(58) Field of Search ....................................... 606/32–50

(56) References Cited

U.S. PATENT DOCUMENTS

6,004,319 A * 12/1999 Goble et al. .................. 606/48
6,328,735 B1 * 12/2001 Curley et al. ................. 606/41

FOREIGN PATENT DOCUMENTS

JP         2000-201946         7/2000

* cited by examiner

*Primary Examiner*—Beverly M. Flanagan
*Assistant Examiner*—Matthew Kasztejna
(74) *Attorney, Agent, or Firm*—Scully, Scott, Murphy & Presser

(57) ABSTRACT

A treatment electrode of a resectoscope apparatus is substantially semicircular-shaped. A length a of a first segment and a length b of a second segment satisfy a relationship of (a>2·b). The first segment is in parallel with the plane on which a parallel lead member exists and has the maximum width of the treatment electrode. The second segment is vertical to the first segment and has the maximum distance between an intersection to the first segment and an intersection to the treatment electrode.

22 Claims, 23 Drawing Sheets a>2b a>2b

RESECTOSCOPE APPARATUS AND ELECTRIC OPERATION APPARATUS

This application claims benefits of Japanese Application No. 2002-112398 filed on Apr. 15, 2002, No. 2002-112393 filed on Apr. 15, 2002, and No. 2002-112394 filed on Apr. 15, 2002, the contents of which are incorporated by this reference.

BACKGROUND OF THE INVENTION

1. Field of the Invention

The present invention relates to a resectoscope apparatus and an electric operation apparatus which incise, resect, and transpire the body tissue through electric resection under an endoscope.

2. Description of the Related Art

Generally, a resectoscope is used for transurethral resection (TUR) and transcervical resection (TCR), and mainly comprises an optical scope (also referred to as a scope) as an endoscope for observation and an electrode unit for resecting the anatomy in an elongated and hollow sheath inserted in the celom.

The resectoscope apparatus includes two types of one for treatment in a non-conductive solution and one for treatment in a conductive solution.

Upon treatment such as the prostatectomy by using the resectoscope apparatus for treatment in the non-conductive solution, the space is expanded by supplying D-sorbitol as an insulative transparent solution corresponding to perfusate for expanding the narrow space and the sheath of the resectoscope is inserted into the space. High-frequency current is energized to a treatment electrode of the electrode unit arranged to the opening of a distal end portion of the sheath while observing a surface of the lesion portion by using the scope arranged in the sheath. The high-frequency current flows to a counter-electrode plate as an external electrode arranged to the outside of the body via the anatomy from the treatment electrode. An operator advances or returns the treatment electrode by operating an operating unit for the treatment of the lesion portion.

In the case of the prostatectomy by using the resectoscope apparatus for treatment in the conductive solution, physiological saline or the like is used for the perfusate as the conductive solution. In the technology disclosed in Japanese unexamined Patent Application Publication No. 2000-201946, a return electrode is arranged near the distal end portion of the elongated and hollow sheath inserted in the celom filled with a conductive solution and the high-frequency current from the treatment electrode is collected via the return electrode.

In the conventional treatment using the return electrode under the conductive solution, bubbles of the conductive solution is generated around the return electrode by energizing the return electrode. The bubbles cover the entire circumference of the electrode and then electric resistance sharply increases between the electrode and the physiological saline and the anatomy and a high voltage is generated, thus to cause the discharging operation. Heat generated due to the discharge operation enables resection, transpiration, and coagulation due to the discharging operation, of the anatomy.

In the resectoscope apparatus using the non-conductive solution, current is concentrated near a metal such as a metal bolt which is implanted in the patient body and the nearby anatomy is baked and the current flows to the nerve in the body. Thus, the patient body reflexively moves and the operator cannot perform the operation. This problem is not caused in the resectoscope apparatus using the conductive solution.

However, in both the above resectoscope apparatuses, the high-frequency current is supplied by turning on a switch of a foot switch by the operator at a certain timing (t0), as shown in FIG. 26, so that the supply power is equal to a constant current value PP (watt) which is predetermined. FIG. 26 is a diagram for explaining a status for supplying power to the resectoscope apparatus.

The constant power value PP is equal to or more than a power value necessary for the treatment for the resection of the anatomy, and the high power equal to or more than the power necessary for the treatment is actually set as output power.

SUMMARY OF THE INVENTION

A resectoscope apparatus comprises: a high-frequency power generating unit which generates high-frequency power for treating the anatomy; a first electrode which supplies to the anatomy, the high-frequency power generated by the high-frequency power generating unit; a solution supply unit which supplies a conductive solution around the electrode; and a second electrode which is arranged in the conductive solution supplied by the solution supply unit and which returns the high-frequency power supplied to the anatomy from the first electrode, wherein the first electrode has two parallel lead members, and a treatment electrode connected to an edge of the parallel lead members, and when a first segment is in parallel with the plane on which the parallel lead members exist and has the maximum width of the treatment electrode and a second segment is vertical to the first segment and has the maximum distance between an intersection to the first segment and an intersection to the treatment electrode, a length a of the first segment and a length b of the second segment satisfy a relationship of (a>2·b).

DESCRIPTION OF THE PREFERRED EMBODIMENTS

Hereinbelow, a description is given of embodiments of the present invention with reference to the drawings.

(First Embodiment)

Figure 1:
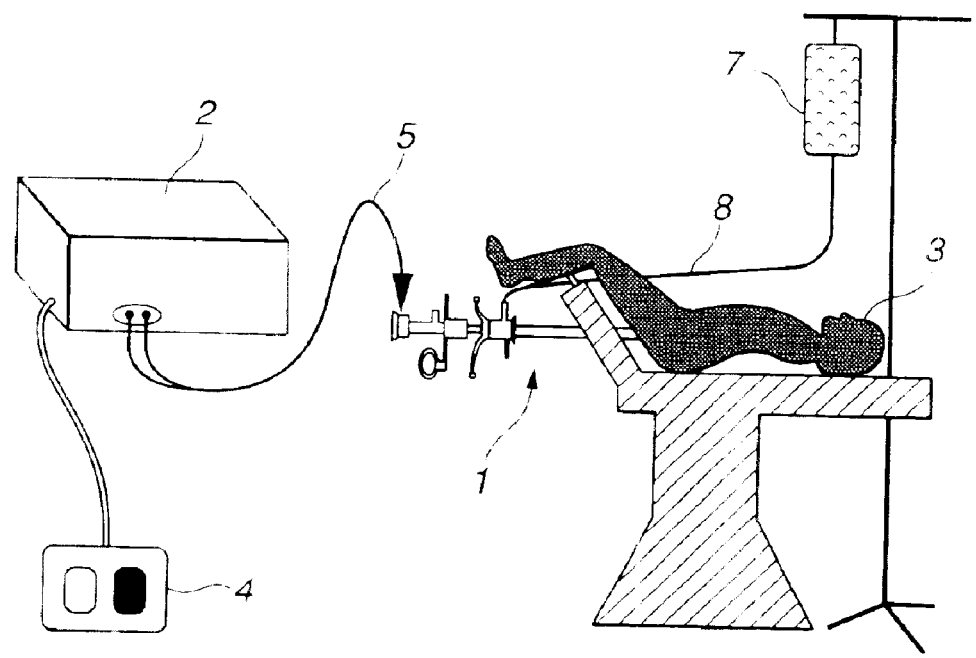
FIG. 1 is a diagram showing the structure of a resectoscope apparatus according to a first embodiment of the present invention.
Figure 2:
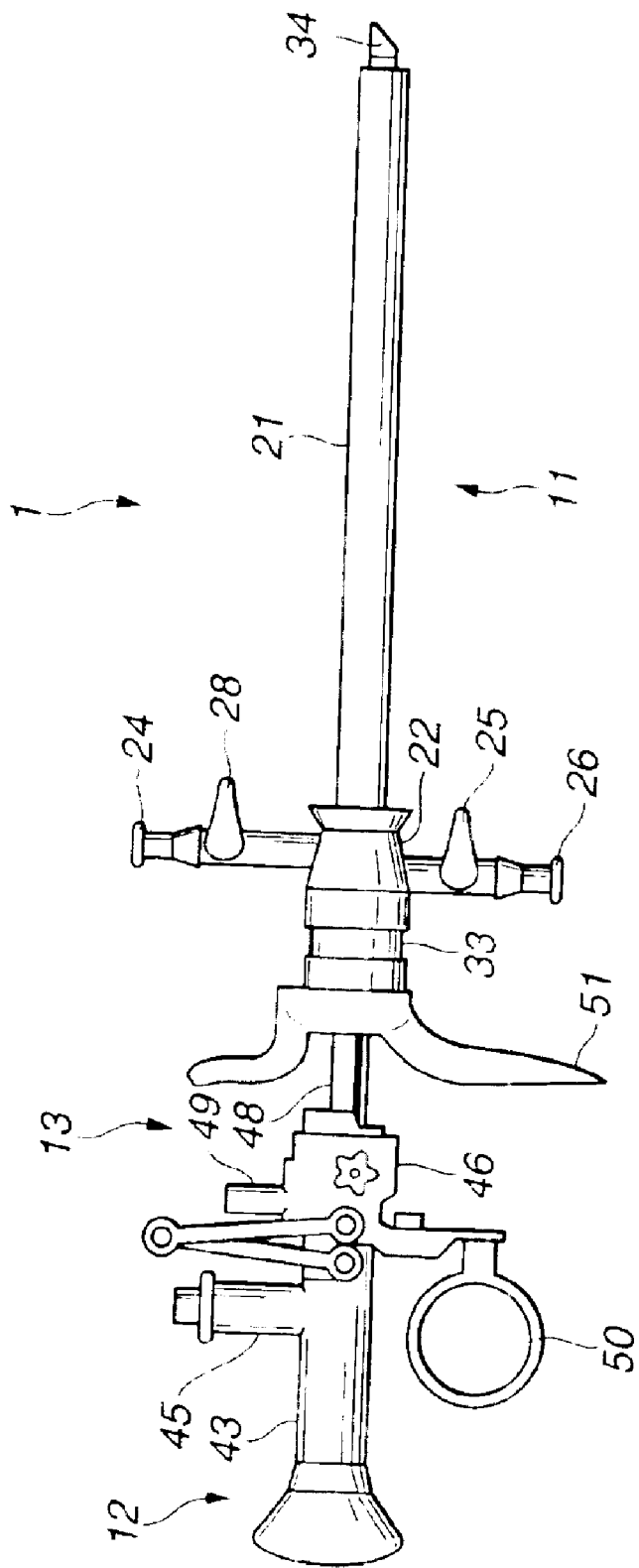
FIG. 2 is a side view showing the structure of the resectoscope shown in FIG. 1.
Figure 3:
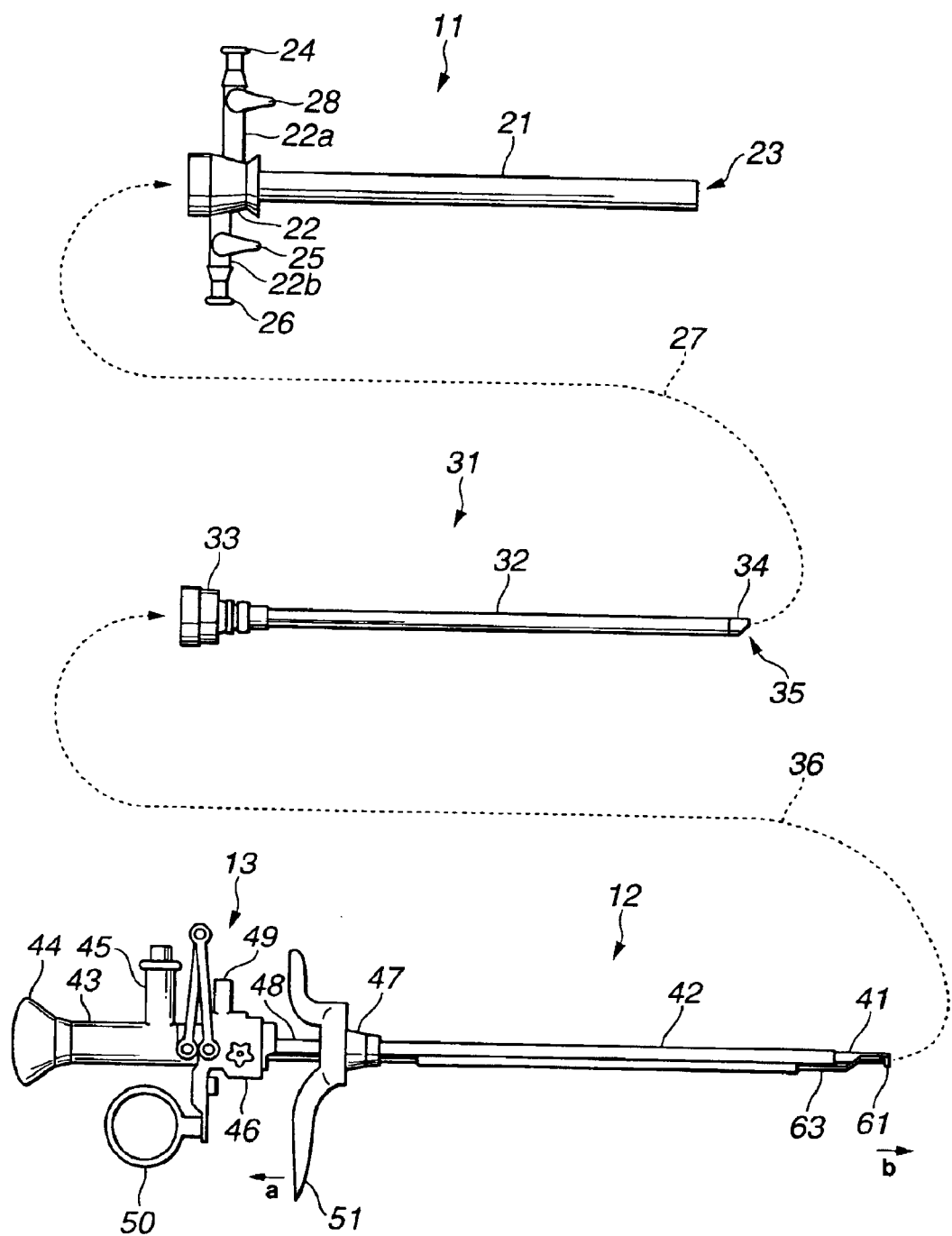
FIG. 3 is an assembly diagram for explaining the structure of a resectoscope 1 shown in FIG. 2.
Figure 4:
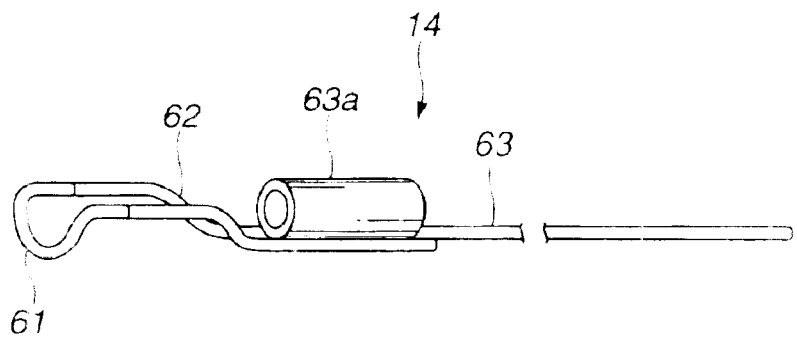
FIG. 4 is a perspective view for explaining the structure of an electrode unit inserted and arranged in an inner sheath shown in FIG. 3.
Figure 5:
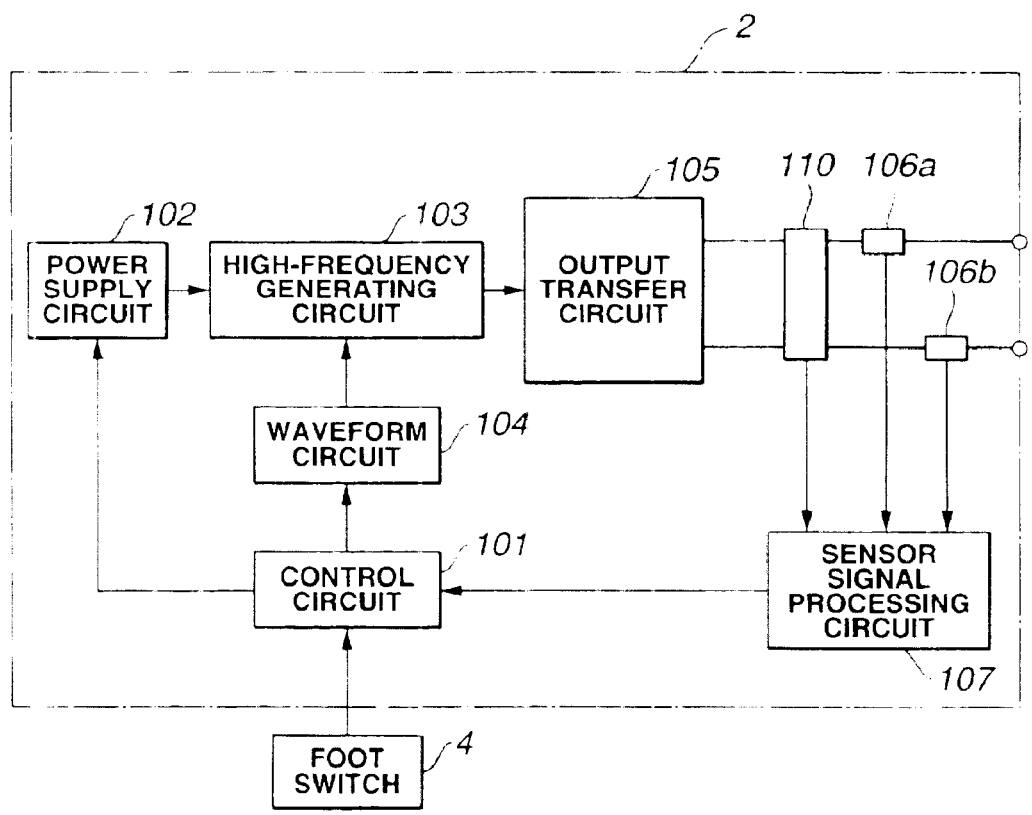
FIG. 5 is a block diagram showing the structure of a high-frequency power supply device shown in FIG. 1.
Figure 6:
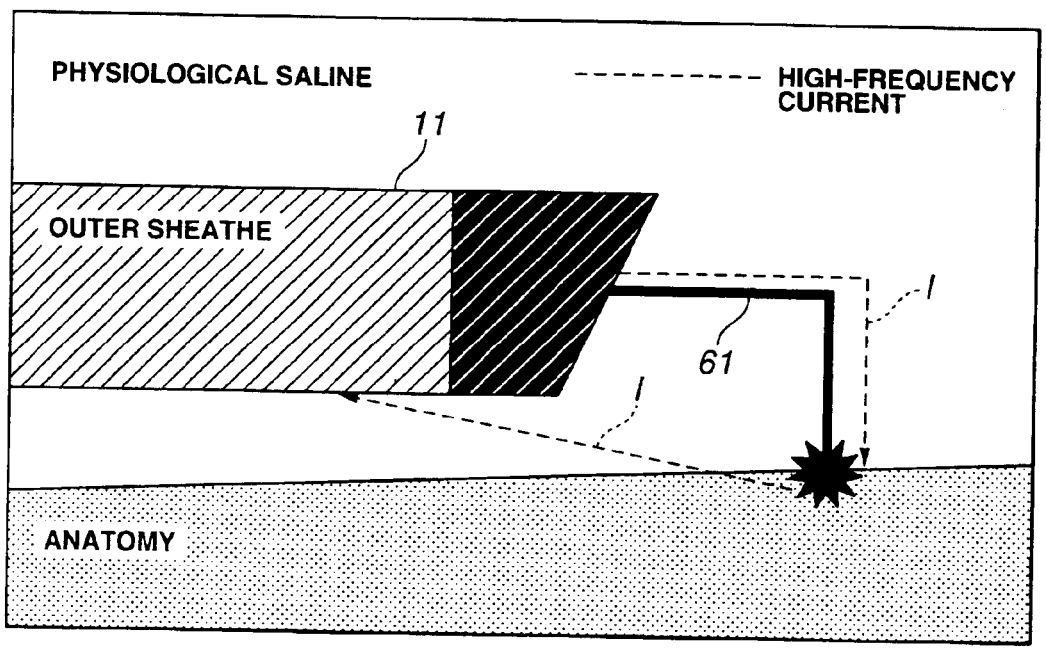
FIG. 6 is a first diagram for explaining the operation of a treatment electrode shown in FIG. 4.
Figure 7:
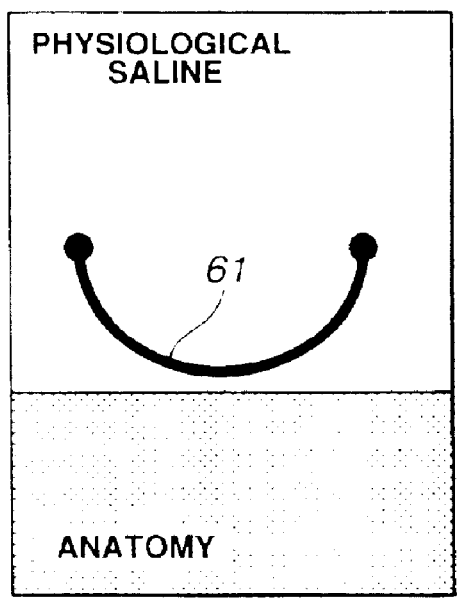
FIG. 7 is a second diagram for explaining the operation of the treatment electrode shown in FIG. 4.
Figure 8:
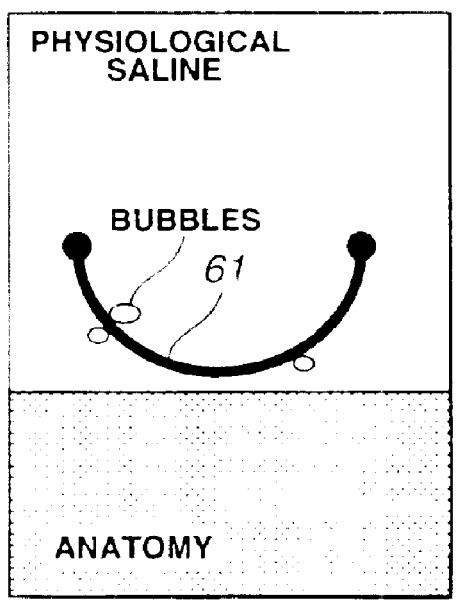
FIG. 8 is a third diagram for explaining the operation of the treatment electrode shown in FIG. 4.
Figure 9:
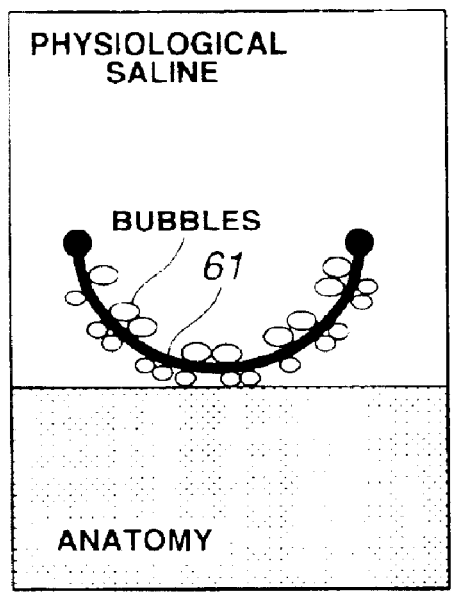
FIG. 9 is a fourth diagram for explaining the operation of the treatment electrode shown in FIG. 4.
Figure 10:
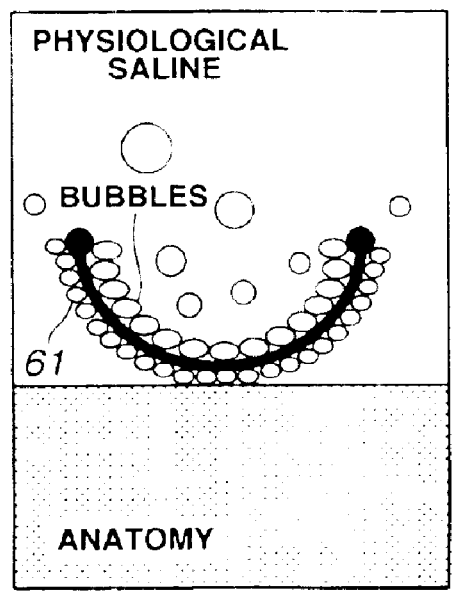
FIG. 10 is a fifth diagram for explaining the operation of the treatment electrode shown in FIG. 4.
Figure 11:
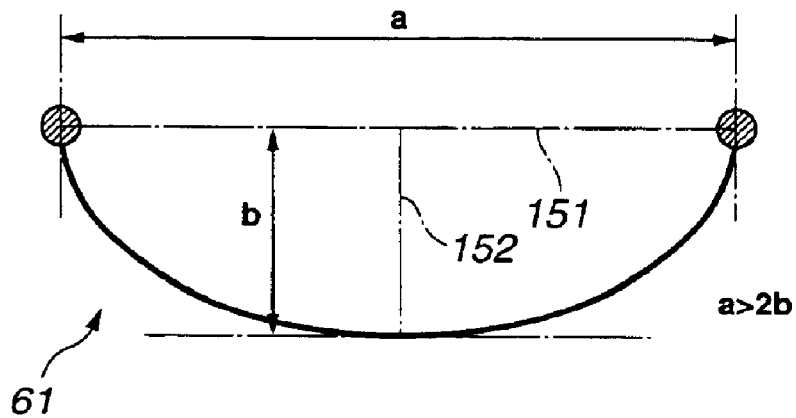
FIG. 11 is a diagram for explaining the shape of an edge of the treatment electrode shown in FIG. 4.
Figure 12:
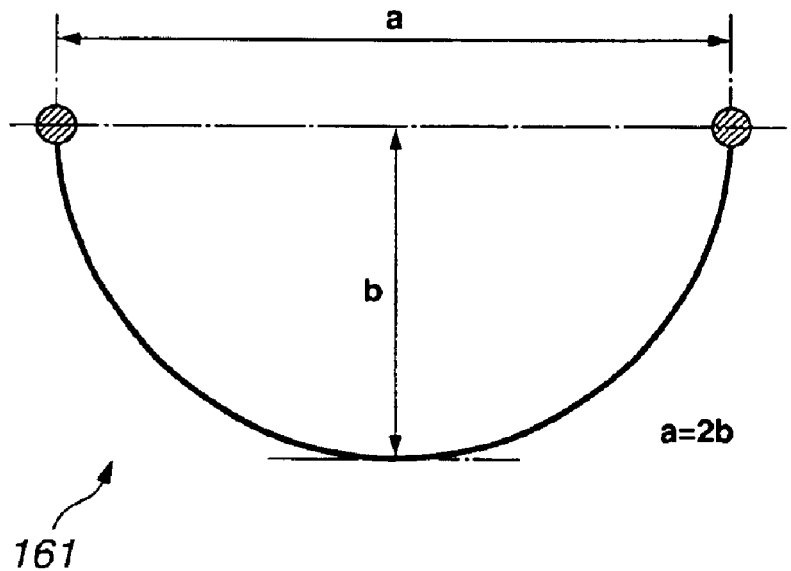
FIG. 12 is a diagram for explaining the shape of an edge of a conventional treatment electrode.
Figure 13:
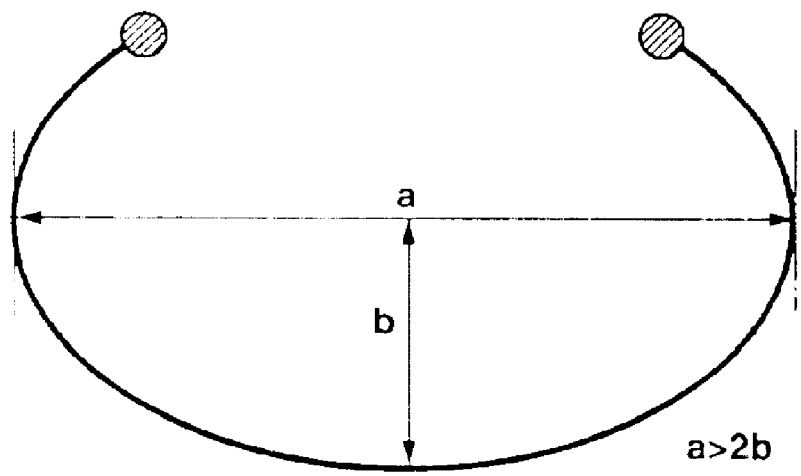
FIG. 13 is a diagram for explaining the shape of an edge of the treatment electrode shown in FIG. 4 according to a first modification.
Figure 14:
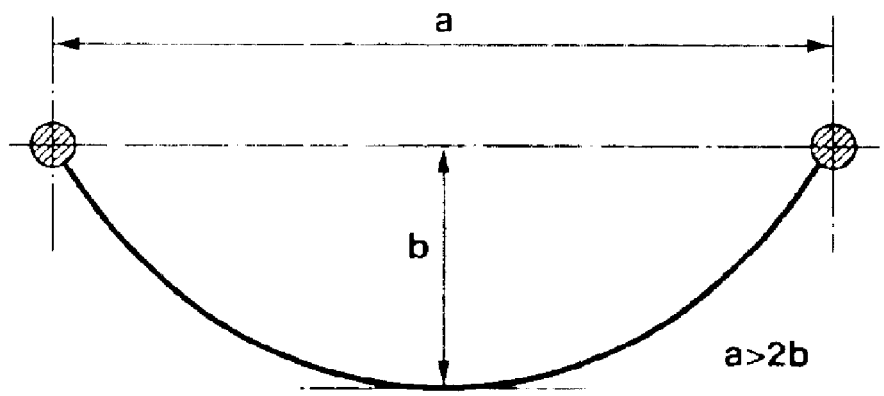
FIG. 14 is a diagram for explaining the shape of an edge of the treatment electrode shown in FIG. 4 according to a second modification.
Figure 15:
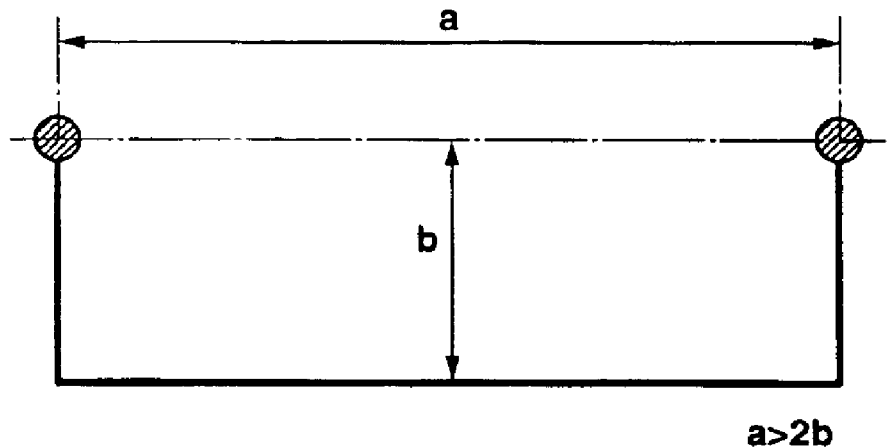
FIG. 15 is a diagram for explaining the shape of an edge of the treatment electrode shown in FIG. 4 according to a third modification.
Figure 16:
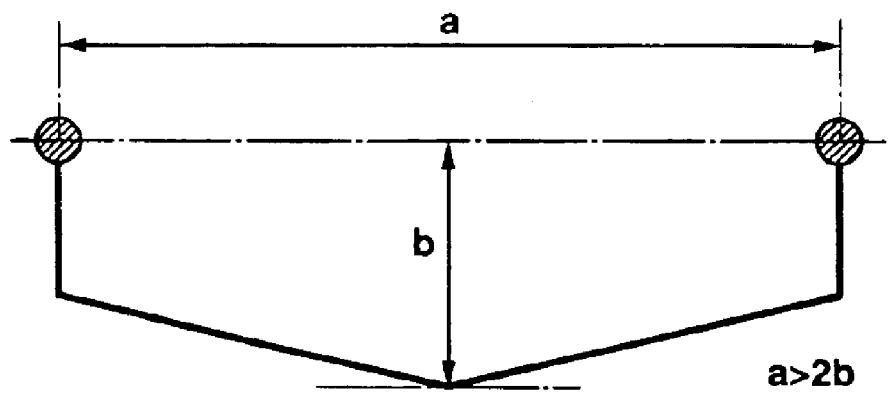
FIG. 16 is a diagram for explaining the shape of an edge of the treatment electrode shown in FIG. 4 according to a fourth modification.

FIGS. 1 to 16 are diagrams according to a first embodiment of the present invention. FIG. 1 is a diagram showing the structure of a resectoscope apparatus, FIG. 2 is a side view showing the structure of a resectoscope shown in FIG. 1, FIG. 3 is an assembly diagram for explaining the structure of a resectoscope 1 shown in FIG. 2, FIG. 4 is a perspective view for explaining the structure of an electrode unit inserted and arranged in an inner sheath shown in FIG. 3, FIG. 5 is a block diagram showing the structure of a high-frequency power supply device shown in FIG. 1, FIG. 6 is a first diagram for explaining the operation of a treatment electrode shown in FIG. 4, FIG. 7 is a second diagram for explaining the operation of the treatment electrode shown in FIG. 4, FIG. 8 is a third diagram for explaining the operation of the treatment electrode shown in FIG. 4, FIG. 9 is a fourth diagram for explaining the operation of the treatment electrode shown in FIG. 4, FIG. 10 is a fifth diagram for explaining the operation of the treatment electrode shown in FIG. 4, FIG. 11 is a diagram for explaining the shape of an edge of the treatment electrode shown in FIG. 4, FIG. 12 is a diagram for explaining the shape of an edge of a treatment electrode shown in FIG. 4 according to a first modification, FIG. 13 is a diagram for explaining the shape of the edge of the treatment electrode shown in FIG. 4 according to a second modification, FIG. 14 is a diagram for explaining the shape of the edge of the treatment electrode shown in FIG. 4 according to a third modification, FIG. 15 is a diagram for explaining the shape of the edge of the treatment electrode shown in FIG. 4 according to a fourth modification, and FIG. 16 is a diagram for explaining the shape of the edge of the treatment electrode shown in FIG. 4 according to a fifth modification.

FIG. 1 shows a status for transurethral resection using the resectoscope apparatus. The resectoscope apparatus comprises a resectoscope 1 and a high-frequency power supply device 2. The resectoscope 1 is connected to the high-frequency power supply device 2 which supplies high-frequency cautery current (hereinafter, referred to as active current) and which collects feedback current (hereinafter, referred to as return current), to/from a treatment electrode of an electrode unit which will be described later. A distal end portion of the resectoscope 1 is transurethrally inserted in a patient 3. A foot switch 4 connected to the high-frequency power supply device 2 is switched on or off to control the power supply to the treatment electrode from the high-frequency power supply device 2. The foot switch 4 is turned on and thus the high-frequency current from the high-frequency power supply device 2 is supplied to the treatment electrode of the resectoscope 1 via a cable 5. The return current is collected to the high-frequency power supply device 2.

Referring to FIG. 1, physiological saline with conductivity as perfusate to the celom such as the bladder is supplied to the resectoscope 1 from a physiological saline pack 7 via a sterilizing tube 8. The operator fills the celom with the physiological saline, then inserts the resectoscope 1 to the celom, moves the treatment electrode to the surface of the anatomy for the incision and resection while viewing the endoscope image for observing the celom, and turns on a switch of the foot switch 4 for the incision.

Next, the structure of the resectoscope 1 will be described with reference to FIGS. 2 to 4. FIG. 2 is a side view showing the structure of the resectoscope 1. FIG. 3 is an assembly diagram for explaining the structure of the resectoscope 1. FIG. 4 is a perspective view for explaining the structure of the treatment electrode.

The resectoscope 1 comprises a hollow outer sheath having a piercing hole as a mantle tube, a scope 12 arranged in the piercing hole of the outer sheath 11, a handle portion 13 as an operating portion, and an electrode unit 14 (refer to FIG. 4) arranged in the piercing hole of the outer sheath 11.

The outer sheath 11 comprises a hollow inserting portion 21 which is inserted in the celom via the urethra, and a proximal main body portion 22 arranged to the rear end of the inserting portion 21. The edge of the inserting portion 21 has an opening portion 23. The proximal main body portion 22 has two fluid tubes 22a and 22b at the side periphery thereof. Specifically, the fluid tube 22a comprises a cock 28 and a solution supply cap 24 which transmit the physiological saline or the like with the conductivity as the perfusate to the treatment portion. The fluid tube 22b comprises a cock 25 and a solution drain cap 26 which drain the physiological saline, or the like.

A tube for transmitting the solution is connected to the solution supply cap 24 as tube connecting means. A tube for draining the solution is connected to the solution drain cap 26 as the tube connecting means. The solution transmission and the solution drain are controlled by moving the cocks 28 and 25.

An inner sheath 31 is inserted from the opening portion of the proximal main body portion 22 on the rear side thereof as shown by a dotted line 27 in FIG. 3 and is arranged in the inserting portion 21. The inner sheath 31 comprises a hollow inserting portion 32 which is inserted in the outer sheath 11, a proximal main body portion 33 arranged to the rear end of the inserting portion 32, and a distal end member 34 which is arranged to the edge of the inserting portion 32 and which is made of a hard resin member as an insulating member. The distal end member 34 comprises an opening portion 35 at the edge thereof. As shown by a dotted line 36 in FIG. 3, the scope 12 is inserted from the opening portion of the proximal main body portion 33 on the rear side thereof, together with the electrode unit 14, and is arranged in the inner sheath 31.

Incidentally, only the inner sheath 31 is attached and used, without using the outer sheath 11.

The scope 12 comprises a hard inserting tube 41 which is inserted and arranged into the elongated inner sheath 31 incorporating an observation optical system, a guide tube 42 to which the inserting tube 41 is inserted, and a proximal portion 43 which is arranged to the base end of the guide tube 42. The proximal portion 43 comprises an ocular portion 44 for operator's visually viewing operation at the base end of the proximal portion 43. The proximal portion 43 comprises, at the side portion thereof, a light guide connecting portion 45 to which a light guide (not shown) for supplying illumination light for observation to an observing portion is connected.

Referring to FIG. 4, the electrode unit 14 inserted and arranged in the inner sheath 31 mainly comprises a treatment electrode 61 arranged to the edge side and made of a hard metal member, parallel lead member 62 to which the treatment electrode 61 is connected at the edge thereof, and an elongated metal pipe 63 to which the proximal portion of the parallel lead member 62 is arranged at the distal end portion. The treatment electrode 61 is elongated and wire-shaped. Reference numeral 63a denotes a stabilizer. The treatment electrode 61 is an elongated wire-shaped electrode. The parallel lead member 62 is a bifurcating member having a parallel portion in the inserting axis of the scope 12. Both end portions of the treatment electrode 61 are connected to a distal end portion of the parallel lead member 62. The treatment electrode 61 is arc-shaped, for example. Further, the treatment electrode 61 and the parallel lead member 62 are hook-shaped at the edge of the electrode unit 14 as an active electrode, and a predetermined angle is set between the plane including the arc treatment electrode 61 and the inserting axis of the scope 12.

The outer periphery of the metal pipe 63 is covered with an insulating tube not shown, and a proximal portion of the metal pipe 63 is exposed to the rear end portion of the insulating tube as an electrode connecting portion.

The electrode unit 14 as the active electrode is arranged in the inner sheath 31 so that the treatment electrode 61 can advance and return in the inserting direction of the inner sheath 31 at the opening portion 35 of the distal end member 35 thereof.

The proximal portion of the metal pipe 63 having the treatment electrode 61 and the parallel lead member 62 on the edge side thereof is inserted in the inserting portion 32 and the proximal main body portion 33 of the inner sheath 31, is extended from the base end surface of the proximal main body portion 33, and is fixed to a slider 46 which will be described later.

Referring back to FIG. 3, the handle portion 13 mainly comprises a sheath connecting portion 47 which is detachably connected to the proximal main body portion 33 of the inner sheath 31, a guide tube 48 which is projected to the back from the rear end surface of the sheath connecting portion 47 and in which the inserting tube 41 is inserted, and the substantially pipe-shaped slider 46 to which the guide tube 48 is slidably held.

The slider 46 comprises an electrode fixing portion (not shown) as an electrically connecting portion to the electrode connecting portion at the rear end portion of the electrode unit 14, a connector 49 for high-frequency power supply which is extended from the high-frequency power supply device 2 and to which the cable 5 for the power supply is detachably connected, and a thumb-hook ring 50 which is ring-shaped and to which the operator's thumb is hooked.

The slider 46 and the sheath connecting portion 47 are connected by an elastic member such as a spring (not shown) so that they are energized to be away from each other. That is, the slider 46 is always energized to the ocular portion 44 by the elastic member.

The operator properly reduces the distance between a finger-hook portion 51 of the sheath connecting portion 47 and the ring 50 while gripping the finger hook portion 51 and the thumb-hook ring 50 arranged to the slider 46, thereby moving the slider 46 in the direction of the edge of the scope 12 with respect to the guide tube 48. The treatment electrode 61 in the electrode unit 14 moves to be projected in the edge direction of the inserting tube 41. When no force acts to the finger-hook portion 51 and the ring 50, the treatment electrode 61 and the distal end portion of the inserting tube 41 are at substantially the same position in the inserting direction of the scope 12. However, when the force acts to the finger-hook portion 51 and the ring 50 in a direction shown by an arrow a in FIG. 3 to reduce the distance, the inserting tube 41 does not move but the treatment electrode 61 moves in a direction shown by an arrow b in FIG. 3 so that it is projected in the edge direction of the scope 12.

On the other hand, the connector 49 for supplying the high-frequency power is electrically connected to the electrode fixing unit by, e.g., lead wiring. Thus, the cable 5 from the high-frequency power supply device 2 is connected to the connector 49 for supplying the high frequency so that it is energized to the treatment electrode 61 in the electrode unit 14 for the treatment of the lesion portion.

The resectoscope apparatus measures leak current by obtaining the difference between the current value supplied to the treatment electrode 61 and the current value of the return current.

Referring to FIG. 5, the high-frequency power supply device 2 comprises a control circuit 101 for receiving a signal from the foot switch 4 and for controlling the power supply, a power supply circuit 102 for generating DC power under the control of the control circuit 101, a high-frequency generating circuit 103 for switching the DC current from the power supply circuit 102 and for generating high-frequency power, a waveform circuit 104 for supplying a waveform signal with the high-frequency power generated by the high-frequency generating circuit 103 under the control of the control circuit 101 to the high-frequency generating circuit 103, an output transfer circuit 105 for amplifying a high-frequency voltage with the high-frequency power generated by the high-frequency generating circuit 103, for applying the amplified voltage between a terminal for the treatment electrode 61 and a terminal for the return current, and for supplying the high-frequency current to the treatment current 61, a voltage sensor 110 for detecting the high-frequency voltage outputted from the output transfer circuit 105, current sensors 106a and 106b for detecting the high-frequency current outputted from the output transfer circuit 105, and a sensor signal processing circuit 107 for A/D converting the voltage values detected by the voltage sensor 110 and the current values detected by the current sensors 106a and 106b. The control circuit 101 controls the power supply circuit 102 and the waveform circuit 104 by calculating the impedance of the anatomy based on digital voltage data and digital current data from the sensor signal processing circuit 107.

Referring to FIG. 6, the treatment electrode 61 is projected from the edge of the resectoscope 1, and high-frequency current I outputted from the processing electrode 61 is collected in the outer sheath 11 via the anatomy and the physiological saline.

FIGS. 7 to 10 show statuses near the treatment electrode 61 arranged to the edge of the resectoscope 1. The energization of the high-frequency current to the treatment electrode 61 starts (FIG. 7). Then, the physiological saline near the treatment electrode 61 is heated by the energy, and bubbles start to be generated (FIG. 8). Further, the energy is continuously supplied and then the amount of bubbles increases and covers the entire circumference of the treatment electrode 61 (FIG. 9). When the bubbles cover the entire circumference of the treatment electrode 61 (FIG. 10), the electric resistance between the treatment electrode 61 and the physiological saline and the anatomy sharply increases and a high voltage is applied. Thus, the discharge operation starts. The heat generated due to the discharge operation enables resection, transpiration, and coagulation due to the discharging operation, of the anatomy.

Next, a description is given of the treatment electrode 61 at the edge of the electrode unit 14 with reference to FIG. 11.

Referring to FIG. 11, the treatment electrode 61 is substantially semicircular and when reference symbol a denotes a length of a segment 151 and reference symbol b denotes a length of a segment 152, a relationship of (a>2·b) is established between the segment 151 and the segment 152.

That is, the segment 151 is in parallel with the plane on which the parallel lead member 62 exists, and has a maximum width of the treatment electrode 61. The segment 152 is vertical to the segment 151, and has a maximum distance between an intersection to the segment 151 and an intersection to the treatment electrode 61. In other words, such a relationship is established that the length a of the segment 151 is longer than twice of the length of the segment 152.

Referring to FIG. 12, in a semicircular treatment electrode 161 similar to the conventional one, the relationship between the length a of the segment 151 and the length b of the segment 152 is (a=2·b). However, according to the first embodiment, it is (a>2·b). Therefore, if the entire length of the treatment electrode 61 is shorted and the discharge operation is caused with lower power in the treatment electrode 61, as compared with the treatment electrode 161 according to the first embodiment, an area for the treatment using the swept treatment electrode 61 is increased and the treatment is efficiently performed.

The shape of the treatment electrode 61 is not limited to that shown in FIG. 11 and the relationship between the length a of the segment 151 and the length b of the segment 152 may satisfy (a>2·b). Thus, the shape of the treatment electrode 61 may be that shown in FIG. 13 or 14.

The shape of the treatment electrode 61 is semicircular and, however, it is not limited to this. The relationship between the length a of the segment 151 and the length b of the segment 152 may satisfy (a>2·b). Thus, the shape of the treatment electrode 61 may be that shown in FIG. 15 or 16.

The electrode unit 14 having the treatment electrode 61 shown in FIGS. 11 to 16 can be exchanged and can be arranged in the inner sheath 31. The electrode unit 14 having the treatment electrode 61 having the proper shape to the treatment portion can selectively be arranged in the inner sheath 31.

As mentioned above, according to the first embodiment, it is advantageous that the discharge operation is performed with lower power and the treatment is effectively executed.

(Second Embodiment)

Figure 17:
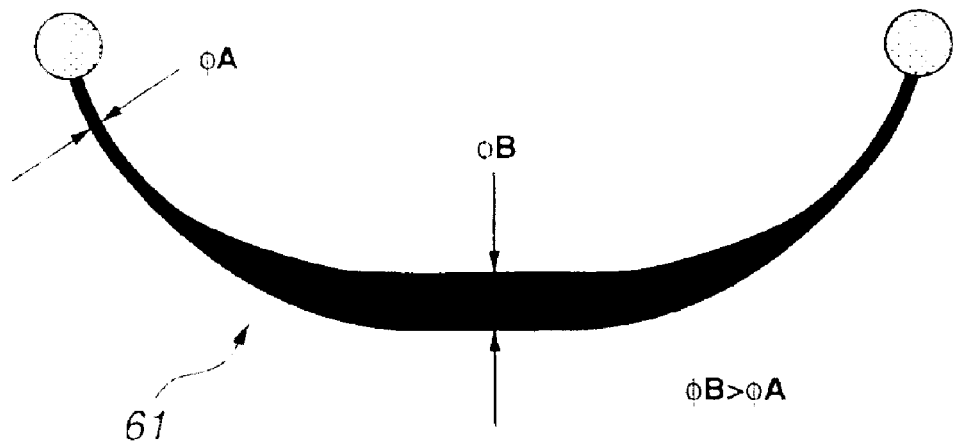
FIG. 17 is a diagram for explaining the shape of an edge of a treatment electrode according to a second embodiment of the present invention.

FIG. 17 is a diagram for explaining the shape of an edge of a treatment electrode according to a second embodiment of the present invention.

The second embodiment is substantially the same as the first embodiment and therefore only different points are described and the same reference numeral denotes the same component.

Referring to FIG. 17, with respect to the treatment electrode 61 according to the second embodiment, a diameter φB of a semicircular bottom end portion is larger than a diameter φA of another portion and the bottom distal end portion is made thick. In other words, the diameter of the treatment electrode 61 is maximum at an intersection between the treatment electrode 61 and the second segment 152 vertical to the first segment 151 having the maximum distance between the intersection of the first segment 151 and the intersection of the treatment electrode 61.

In addition to the advantages according to the first embodiment, the diameter φB of the semicircular bottom end portion is larger than the diameter φA of the other portion in the treatment electrode 61. Therefore, when the high-frequency current flows from the treatment electrode 61 and the resection is performed, the bottom end portion of the treatment electrode 61 can resect similarly to the resection of the other portion.

The diameter of the bottom end portion in the treatment electrode 61 becomes thinner and this portion is easily disconnected due to the wearing caused by the resection of the bottom end portion in the treatment electrode 61. The life of the treatment electrode 61 depends on the diameter of the bottom end portion of the treatment electrode 61. However, since the diameter ϕB of the semicircular bottom end portion is larger than the diameter ϕA of the other portion according to the second embodiment, the life of the treatment electrode 61 is elongated.

As mentioned above, advantageously, the discharge operation is performed with lower power and the treatment is effectively executed according to the second embodiment.

(Third Embodiment)

Figure 18:
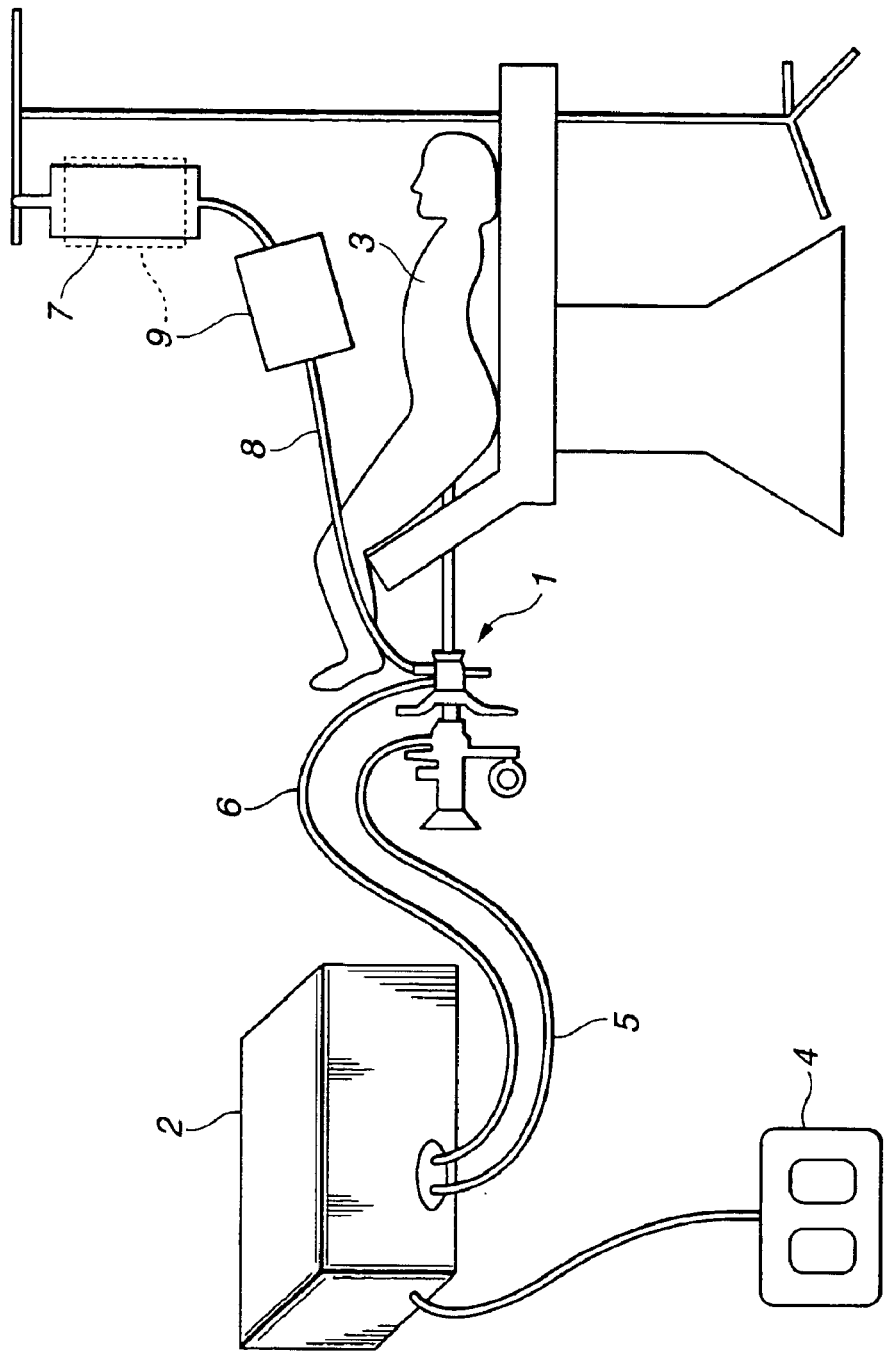
FIG. 18 is a diagram for explaining the structure of an electric operation apparatus using a resectoscope apparatus according to a third embodiment of the present invention.

FIG. 18 is a diagram for explaining the structure of an electric operation apparatus using a resectoscope apparatus. The same reference numerals according to the first embodiment denote the same components.

FIG. 18 shows a status for transurethral resection using the resectoscope apparatus. The resectoscope apparatus comprises the resectoscope 1 and the high-frequency power supply device 2. The resectoscope 1 is connected to the high-frequency power supply device 2 which supplies the high-frequency cautery current (hereinafter, referred to as active current) and which collects feedback current (hereinafter, referred to as return current), to/from the treatment electrode of the electrode unit which will be described later. The distal end portion of the resectoscope 1 is transurethrally inserted in the patient 3. The foot switch 4 connected to the high-frequency power supply device 2 is switched on or off to control the power supply to the treatment electrode from the high-frequency power supply device 2. The foot switch 4 is turned on and thus the high-frequency current from the high-frequency power supply device 2 is supplied to the treatment electrode of the resectoscope 1 via the cable 5. The return current is collected via the cable 6, which will be described later.

Referring to FIG. 18, physiological saline with conductivity as perfusate to the celom such as the bladder is supplied to the resectoscope 1 from the physiological saline pack 7 via the sterilizing tube 8. A heater 9 is arranged to surround the outer periphery of the sterilizing tube 8 in the halfway of the sterilizing tube 8. The heater 9 heats the physiological saline to a set temperature by temperature control means (not shown). Incidentally, the heater 9 may be arranged to surround the physiological saline pack 7 as shown by a dotted line in FIG. 18. The heater 9 is detachably attached to the sterilizing tube. The operator fills the celom with the physiological saline, then inserts the resectoscope 1 to the celom, moves the treatment electrode to the surface of the anatomy for the incision and resection while viewing the endoscope image for observing the celom, and turns on the switch of the foot switch 4 for the incision.

Figure 19:
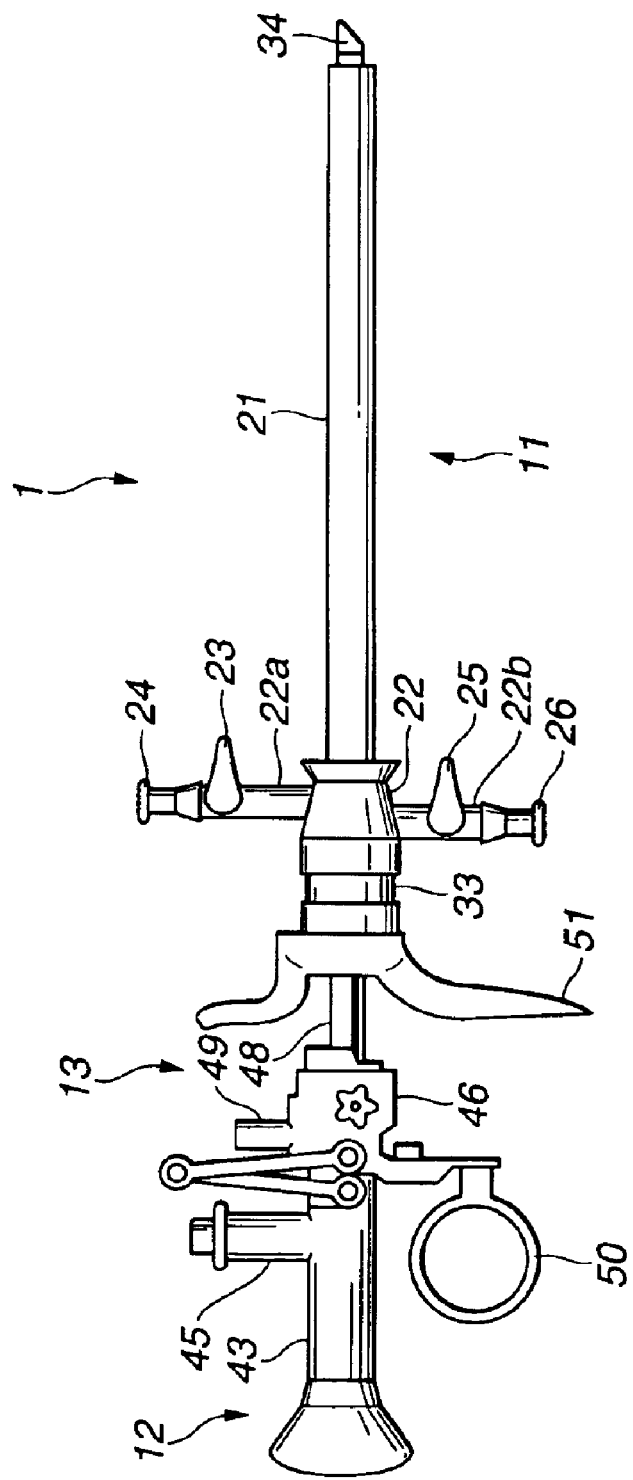
FIG. 19 is a side view showing the structure of a resectoscope according to the third embodiment.
Figure 20:
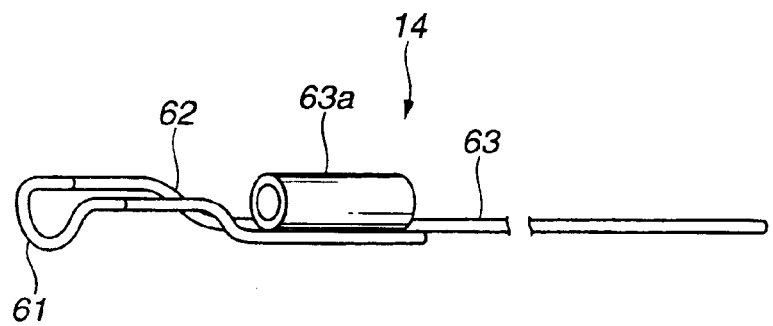
FIG. 20 is a perspective view for explaining the structure of an electrode according to the third embodiment.
Figure 21:
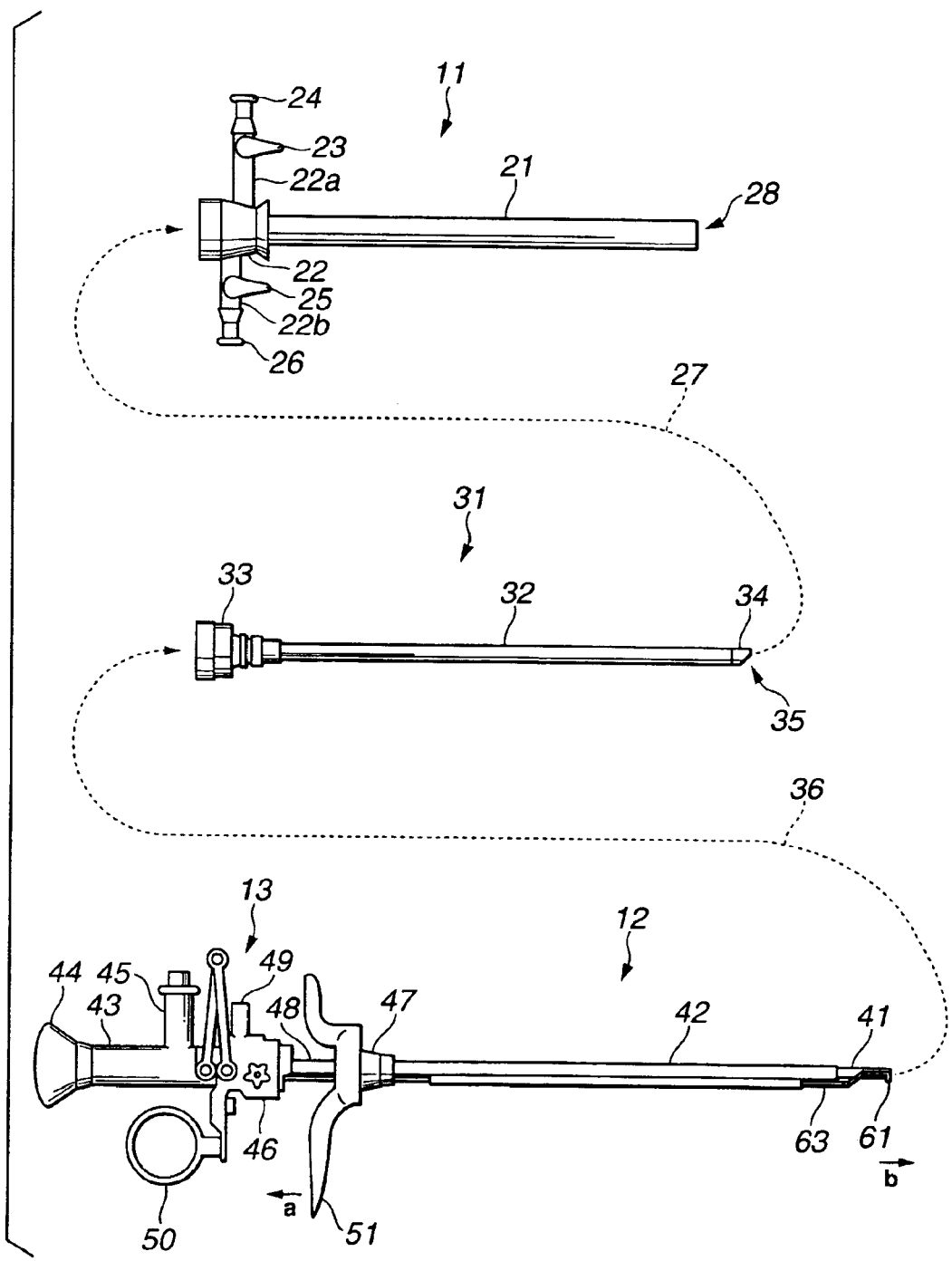
FIG. 21 is an assembly diagram for explaining the structure of the resectoscope according to the third embodiment.

Next, the structure of the resectoscope 1 will be described with reference to FIGS. 19 to 21. FIG. 19 is a side view showing the structure of the resectoscope 1. FIG. 20 is a perspective view for explaining the structure of the treatment electrode. FIG. 21 is an assembly diagram for explaining the structure of the resectoscope 1.

The resectoscope 1 comprises the hollow outer sheath 11 having the piercing hole as the mantle tube, the scope 12 arranged in the piercing hole of the outer sheath 11, the handle portion 13 as an operating portion, and the electrode unit 14 arranged in the piercing hole of the outer sheath 11.

The outer sheath 11 comprises the hollow inserting portion 21 which is inserted in the celom via e.g. the urethra, and the proximal main body portion 22 arranged to the rear end of the inserting portion 21. The edge of the inserting portion 21 has the opening portion 28. The proximal main body portion 22 has two fluid tubes 22a and 22b at the side periphery thereof. Specifically, the fluid tube 22a comprises a cock 23 and a solution supply cap 24 which transmit the physiological saline or the like with the conductivity as the perfusate to the treatment portion. The fluid tube 22b comprises a cock 25 and a solution drain cap 26 which drain the physiological saline. A tube for transmitting the solution is connected to the solution supply cap 24 as the tube connecting means. A tube for draining the solution is connected to the solution drain cap 26 as the tube connecting means. The solution transmission and the solution drain are controlled by moving the cocks 23 and 25.

The inner sheath 31 is inserted from the opening portion of the proximal main body portion 22 on the rear side thereof as shown by a dotted line 27 in FIG. 21 and is arranged in the inserting portion 21. The inner sheath 31 comprises the hollow inserting portion 32 which is inserted in the outer sheath 11, the proximal main body portion 33 arranged to the rear end of the inserting portion 32, and a distal end member 34 which is arranged to the edge of the inserting portion 32 and which is made of a hard resin member as an insulating member. The distal end member 34 comprises the opening portion 35 at the edge thereof. As shown by a dotted line 36 in FIG. 21, the scope 12 is inserted from the opening portion of the proximal main body portion 33 on the rear side thereof, together with the electrode unit 14, and is arranged in the inner sheath 31.

Incidentally, only the inner sheath 31 is attached and used, without using the outer sheath 11.

The scope 12 comprises the hard inserting tube 41 which is inserted and arranged into the elongated inner sheath 31 incorporating the observation optical system, the guide tube 42 to which the inserting tube 41 is inserted, and a proximal portion 43 which is arranged to the base end of the guide tube 42. The proximal portion 43 comprises the ocular portion 44 for operator's visually viewing operation at the base end of the proximal portion 43. The proximal portion 43 comprises, at the side portion thereof, a light guide connecting portion 45 to which a light guide (not shown) for supplying illumination light for observation to an observing portion is connected.

Referring to FIG. 20, the electrode unit 14 inserted and arranged in the inner sheath 31 mainly comprises the treatment electrode 61 arranged to the edge side and made of a hard metal member, the bifurcating arm member 62, and an elongated metal pipe 63 which is extended from a proximal portion of the bifurcating arm portion 62 to the rear side thereof. The treatment electrode 61 is elongated and wire-shaped. The bifurcating arm member 62 is a bifurcating member having a parallel portion in the inserting axis of the scope 12. Both end portions of the treatment electrode 61 are connected to a distal end portion of the bifurcating member. The processing electrode 61 is arc-shaped. Further, the treatment electrode 61 and the bifurcating arm member 62 are hook-shaped at the edge of the electrode unit 14 as an active electrode, and a predetermined angle is set between the plane including the arc treatment electrode 61 and the inserting axis of the scope 12.

The outer periphery of the metal pipe 63 is covered with an insulating tube (not shown), and the proximal portion of the metal pipe 63 is exposed to the rear end portion of the insulating tube as an electrode connecting portion.

The electrode unit 14 as the active electrode is arranged in the inner sheath 31 so that the treatment electrode 61 can advance and return in the inserting direction of the inner sheath 31 at the opening portion 35 of the distal end member 34 thereof.

The proximal portion of the metal pipe 63 having the treatment electrode 61 and the bifurcating arm member 62 on the edge side thereof is inserted in the inserting portion 32 and the proximal main body portion 33 of the inner sheath 31, is extended from the base end surface of the proximal main body portion 33, and is fixed to the slider 46 which will be described later.

The handle portion 13 mainly comprises the sheath connecting portion 47 which is detachably connected to the proximal main body portion 33 of the inner sheath 31, the guide tube 48 which protrudes from the rear end surface of the sheath connecting portion 47 rearward and in which the inserting tube 41 is inserted, and the substantially pipe-shaped slider 46 to which the guide tube 48 is slidably held.

The slider 46 comprises the electrode fixing portion (not shown) as an electrically connecting portion to the electrode connecting portion at the rear end portion of the electrode unit 14, the connector 49 for high-frequency power supply which is extended from the high-frequency power supply device 2 and to which the cable 5 for the power supply is detachably connected, and the thumb-hook ring 50 which is ring-shaped and to which the operator's thumb is hooked.

The slider 46 and the sheath connecting portion 47 are connected by an elastic member such as a spring (not shown) so that they are energized to be away from each other. That is, the slider 46 is always energized to the ocular portion 44 by the elastic member.

The operator properly reduces the distance between the finger-hook portion 51 of the sheath connecting portion 47 and the ring 50 while gripping the finger-hook portion 51 and the thumb-hook ring 50 arranged to the slider 46, thereby moving the slider 46 in the direction of the edge of the scope 12 with respect to the guide tube 48. The treatment electrode 61 in the electrode unit 14 moves to be projected in the edge direction of the inserting tube 41. When no force acts to the finger-hook portion 51 and the ring 50, the treatment electrode 61 and the distal end portion of the inserting tube 41 are at substantially the same position in the inserting direction of the scope 12. However, when the force acts to the finger-hook portion 51 and the ring 50 in a direction shown by an arrow a in FIG. 21 to reduce the distance, the inserting tube 41 does not move but the treatment electrode 61 moves in a direction shown by an arrow b in FIG. 21 so that it is projected in the edge direction of the scope 12.

The connector 49 for supplying the high-frequency power is electrically connected to the electrode fixing unit by, e.g., lead wiring. Thus, the cable 5 connected to the high-frequency power supply device 2 is connected to the connector 49 for supplying the high frequency so that it is energized to the treatment electrode 61 in the electrode unit 14 for the treatment of the lesion portion. The resectoscope apparatus measures leak current by obtaining the difference between the current value supplied to the treatment electrode 61 and the current value of the return current.

Figure 22:
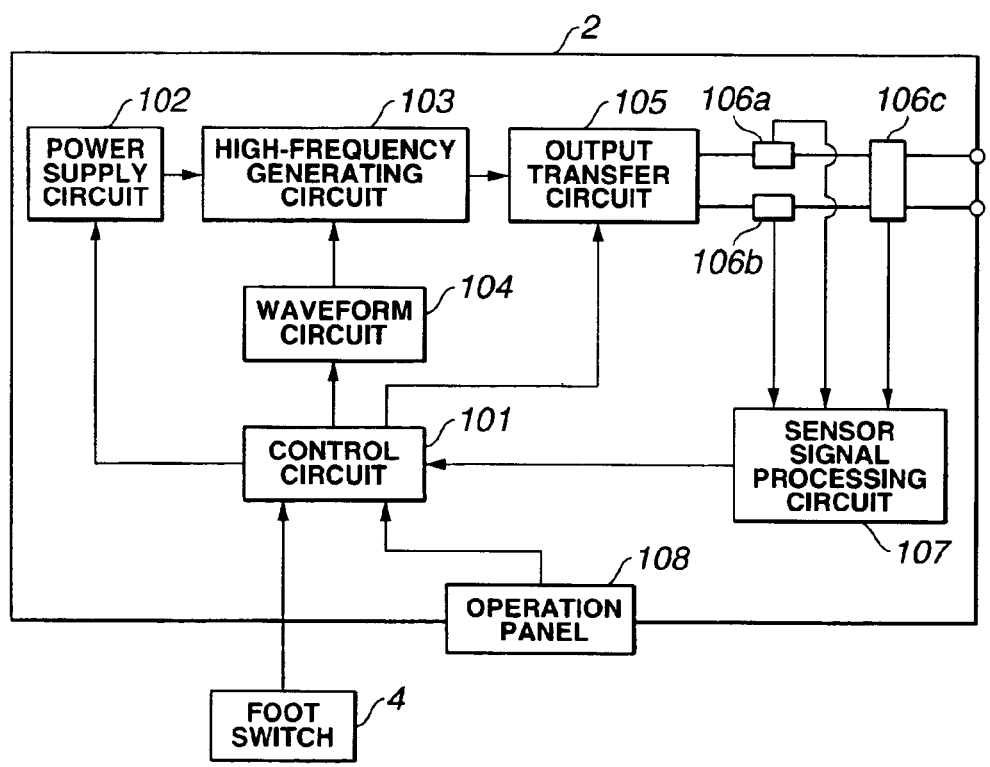
FIG. 22 is a block diagram showing the structure of a high-frequency power supply device according to the third embodiment.

FIG. 22 is a block diagram showing the structure of the high-frequency power supply device.

Referring to FIG. 22, the high-frequency power supply device 2 comprises the control circuit 101 for receiving the signal from the foot switch 4 and for controlling the power supply, the power supply circuit 102 for generating DC power under the control of the control circuit 101, the high-frequency generating circuit 103 for switching DC current from the power supply circuit 102 and for generating high-frequency power, the waveform circuit 104 for supplying a waveform signal with the high-frequency power generated by the high-frequency generating circuit 103 under the control of the control circuit 101 to the high-frequency generating circuit 103, the output transfer circuit 105 for amplifying the high-frequency voltage with the high-frequency power generated by the high-frequency generating circuit 103, for applying the amplified voltage between the terminal for the treatment electrode 61 and the terminal for the return current, and for supplying the high-frequency current to the treatment current 61, the current sensors 106a and 106b for detecting the high-frequency current outputted from the output transfer circuit 105, a voltage sensor 106c for detecting the voltage between the terminal of the treatment electrode 61 and the terminal for the return current, and the sensor signal processing circuit 107 for A/D converting the current values detected by the current sensors 106a and 106b and the voltage value detected by the voltage sensor 106c. The control circuit 101 controls the power supply circuit 102, the waveform circuit 104, and the output transfer circuit 105 based on digital current data and digital voltage data from the sensor signal processing circuit 107.

The control circuit 101 includes a calculating device such as a CPU (Central Processing Unit) and executes the control operation, which will be described later, by software. The control circuit 101 may be realized by a hardware circuit which is not software.

Figure 23:
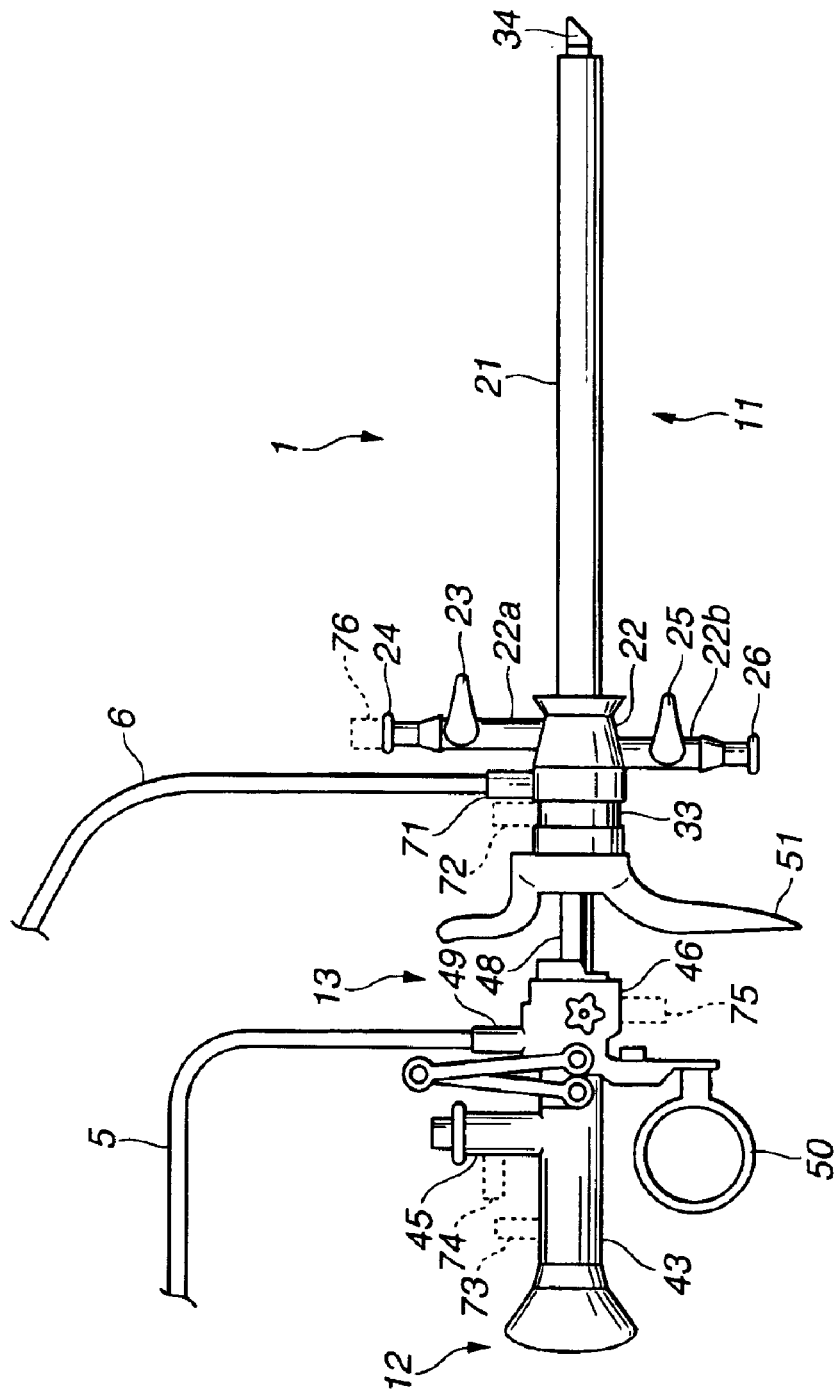
FIG. 23 is a side view showing the structure of the resectoscope having a connector for connection to a cable for return current according to the third embodiment.

A specific description is given of means for collecting the return current in the above-described resectoscope apparatus. According to the third embodiment, the return current is collected without using the conventional opposite-electrode plate and methods for collecting the return current exist. The methods are described with reference to FIG. 23. FIG. 23 is a side view for explaining the structure of the resectoscope 1 having a connector for connection to a cable for the return cable.

(1) Collection of the return current via the outer sheath

Referring to FIG. 23, a cable connector 71 for the return current is arranged to the proximal main body portion 22 of the outer sheath 11.

The inserting portion 21 and the proximal main body portion 22 of the outer sheath 11 are made of a conductive member such as metal and, therefore, the current from the active electrode flows to the outer sheath 11 via the conductive solution and further flows to the connector 71 as electrically connecting means to the cable 6 for the return current. Thus, the return current is collected to the cable 6 for the return cable via the outer sheath 11.

When the return current is collected via the outer sheath, if the anatomy touches the outer sheath 11, the return current is collected via the metal member due to the difference in impedance.

(2) Collection of the return current via the inner sheath

As shown in FIG. 23, a cable connector 72 for the return current shown by a dotted line may be arranged to the proximal main body portion 33 of the inner sheath 31.

In this case, the inserting portion 32 and the proximal main body portion 33 in the inner sheath 31 are made of a conductive member such as metal. Thus, the current from the active electrode flows to the inner sheath 31 via the conductive solution and further flows to the connector 72 as electrically connecting means to the cable 6 for the return current. Therefore, the return current is collected to the cable 6 for the return current via the inner sheath 31.

(3) Collection of the return current via the scope

As shown in FIG. 23, a cable connector 73 for the return current shown by a dotted line may be arranged to the proximal portion 43 of the scope 12.

In this case, the guide tube 42, the sheath connecting portion 47, the guide tube 48, the slider 46, and the proximal portion 43 are made of the conductive member such as metal. The current from the active electrode flows to the scope 12 via the conductive solution and further flows to the connector 73 as the electrically connecting means to the cable 6 for the return current. Therefore, the return current is collected to the cable 6 for the return current via the scope 12.

As shown by a dotted line 74, the connector may be arranged to the light guide connecting portion 45 of the scope 12.

(4) Collection of the return current via the handle portion

As shown in FIG. 23, a cable connector 75 for the return current shown by a dotted line may be arranged to the slider 46 of the handle portion 13.

The connector 75 is electrically connected to the guide tube 48 as the conductive member such as the metal in the handle portion 13. Further, the guide tube 48 is electrically connected to the outer sheath 11, the inner sheath 31, or the scope 12.

Therefore, the current from the active electrode flows to the handle portion 13 via the outer sheath 11, the inner sheath 31, or the scope 12, and further flows to the cable 6 for the return current via the connector 75 as the electrically connecting means to the cable 6 for the return current. Therefore, the return current is collected to the cable 6 via the handle portion 13.

(5) Collection of the return current via the fluid tube

As shown in FIG. 23, a cable connector 76 for the return current shown by a dotted line may be arranged to the solution supply cap 24 provided for the outer sheath 11. The solution supply cap 24 is arranged to the distal end portion of the solution supply tube provided for the outer sheath 11.

In this case, the inserting portion 21, the proximal main body portion 22, and the fluid tube 22a are made of the conductive member such as metal. The current from the active electrode flows to the fluid tube 22a via the conductive solution and further flows to the connector 76 as the electrically connecting means to the cable 6 for the return current. Therefore, the return current is collected to the cable 6 for the return current via the fluid tube.

Although the solution supply cap 24 has the connector 76, the solution drain cap 26 may have the connector 76.

Further, although the connector is arranged to the solution supply cap 24 or the solution drain cap 26, independently, as mentioned above, the shape of the solution supply cap 24 or the solution drain cap 26 is not changed and either one may be used as the connector 76 for the return current so as to collect the return current.

The above connectors 71 to 76 are fixed to the inner sheath 31 and so forth, however, they may be detachable to the inner sheath 31 and so on.

With the above structure, the return current is collected without the arrangement of the return electrode near the distal end portion of the sheath in the related art. Consequently, the structure of the resectoscope is simple, and the diameter of the inserting portion is not thick.

As a method for collecting the return current, as disclosed in Japanese unexamined Patent Application Publication No. 2000-201946, the return electrode as the means for collecting the return current may be arranged near the distal end portion of the elongated and hollow sheath inserted in the celom and the high-frequency current from the treatment electrode may be collected via the return electrode.

When the treatment using the conductive solution is performed by using the resectoscope apparatus having the connector for connection to the return cable, the cable 6 for the return current may be connected to the connector arranged to the outer sheath and so forth as shown in FIGS. 18 and 23.

Next, a description is given of an output status of the output power from the high-frequency power supply device 2.

Figure 24:
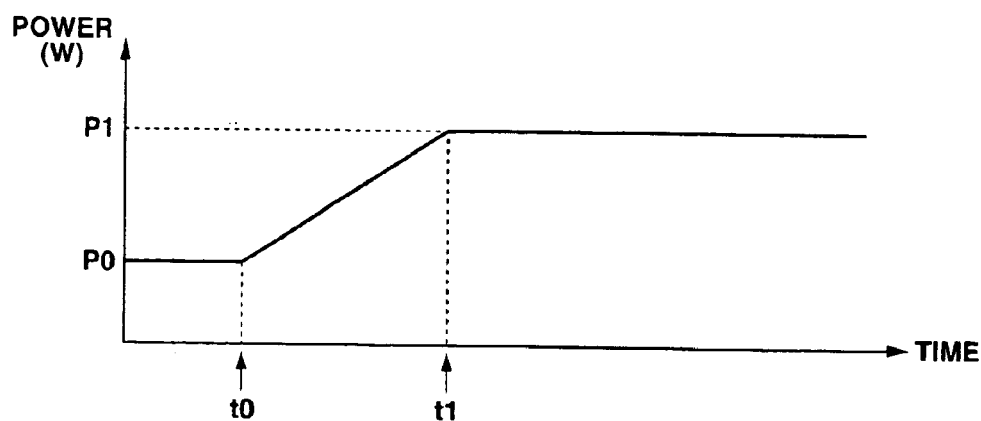
FIG. 24 is a diagram showing a status of one temporal change in output power from the high-frequency power supply device according to the third embodiment.

FIG. 24 is a diagram showing one example of a status of the temporal change in output power from the high-frequency power supply device when the operator switches on the foot switch 4. The axis of ordinate denotes the output power and the axis of abscissa denotes time. The operator presses the foot switch 4 at certain time, namely, at time t0 and then the control circuit 101 controls the power supply circuit 102, the waveform circuit 104, and the output transfer circuit 105 so as to gradually increase the output power, that is, a value P0 as 0 watt, as shown in FIG. 24.

The control circuit 101 controls a voltage value or a current value of the power supply circuit 102, the waveform circuit 104, or the amplification of the output transfer circuit 105, thus to increase the output power. As a result, the control circuit 101 gradually increases the power as shown in FIG. 24.

The control circuit 101 gradually increases the power and simultaneously monitors by using the treatment electrode 61 whether or not the discharge operation is caused. Specifically, the output power gradually increases to a higher current value from a lower current value and then the physiological saline evaporates at certain time (t1) to generate steam. Further, the resistance of the treatment electrode 61 increases and the discharge operation starts. This discharge operation enables the resection of the anatomy. Therefore, the control circuit 101 detects the start of the discharge operation, then, stops the increase of the output power, and holds the output power to a constant value, as P1 watt, of the output power upon detecting the discharge operation.

Once the discharge operation starts, the power does not need to increase any more. Thus, the output power may increase to P1 watt as the minimum power value. Accordingly, the electric operation is realized by using the resectoscope apparatus without unnecessary power consumption.

Figure 25:
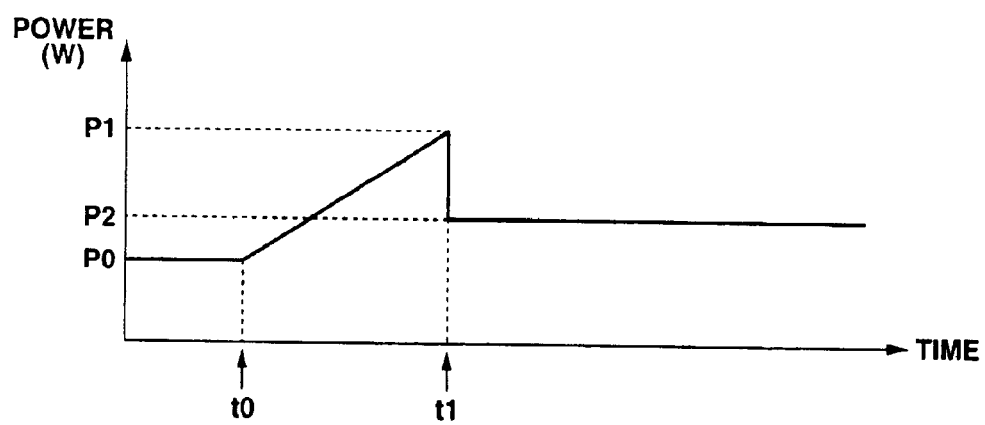
FIG. 25 is a diagram showing a status of another temporal change in output power from the high-frequency power supply device according to the third embodiment.
Figure 26:
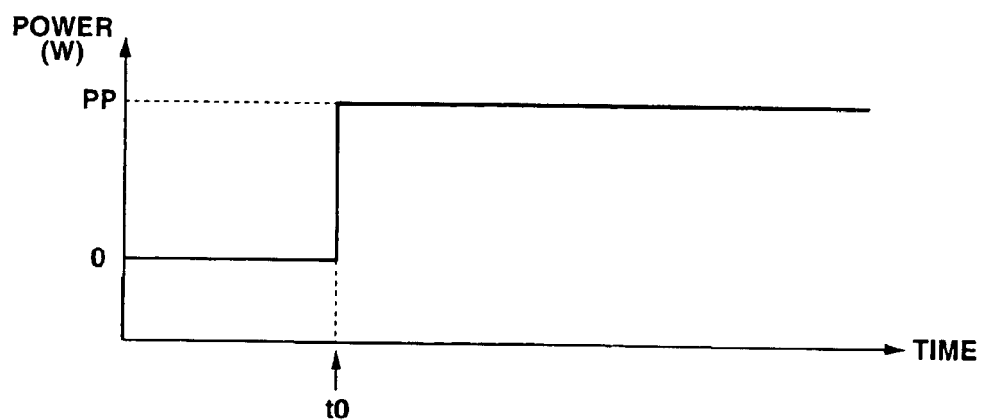
FIG. 26 is a diagram for explaining a status for supplying power to the conventional resectoscope apparatus.

FIG. 25 is a diagram showing another example of the status of the temporal change in output power from the high-frequency power supply device. The axis of ordinate denotes the output power and the axis of abscissa denotes time. The operator presses the foot switch 4 at certain time, namely, at time t0 and then the control circuit 101 controls the power supply circuit 102, the waveform circuit 104, and the output transfer circuit 105 so as to gradually increase the output power, that is, a value P0 as 0 watt, as shown in FIG. 25.

The control circuit 101 gradually increases the power and simultaneously monitors by using the treatment electrode 61 whether or not the discharge operation is caused. Specifically, the output power gradually increases to a higher current value from a lower current value and then the physiological saline evaporates at certain time (t1) to generate steam. Further, the resistance of the treatment electrode 61 increases and the discharge operation starts.

The control circuit 101 detects the start of the discharge operation, then, stops the increase of the output power, reduces the output power P1 watt upon detecting the discharge operation to a constant value P2 which is preset, lower than P1 watt, and holds the constant value P2.

When the physiological saline evaporates at the output power of 220 to 300 watt, that is, when the evaporation is detected, the power is thereafter reduced. After the discharge operation, lower power, e.g. 100 watt may be held. Once the discharge operation starts in the treatment electrode 61, steam is continuously generated at the power of 100 watt because the power is low but large heat is generated. In other words, the temperature of the treatment electrode 61 first increases at the power of 300 watt and, however, the output power may thereafter be reduced.

It is determined whether or not the discharge operation starts by calculating the impedance based on the voltage value and the current value detected by the voltage sensor 106c and the current sensors 106a and 106b. For example, it is determined whether or not the output power is reduced to a constant value depending on whether or not the resistance of the anatomy becomes the impedance which is preset, e.g., 500Ω.

Once the discharge operation starts, the power does not need to increase any more. Thus, the output power may increase to P1 watt as the minimum power value. Accordingly, the electric operation is realized by using the resectoscope apparatus without unnecessary power consumption.

The output power may be supplied because the discharge operation is possible when the conductive solution is filled in the celom and the active electrode and the return electrode are normally held in the conductive solution. However, when the conductive solution is not filled in the celom or when the active electrode and the return electrode are not normally held in the conductive solution, the discharge operation starts in an incomplete status.

Then, impedance measuring means detects that prior to the supply of the high-frequency current for discharge operation to the active electrode, the conductive perfusate is fully filled in the lesion portion and the active electrode and the return electrode are normally held in the conductive solution. Further, the high-frequency current is supplied to the active electrode based on the detected result.

Hence, the impedance is calculated based on the output signal from the voltage sensor and the current sensor while outputting the preset low output power. Then, when the impedance is equal to the preset value or less, the high-frequency current is supplied and when the impedance is over the preset value, the high-frequency current is not supplied. If the impedance is e.g., 50Ω or less as the preset output value, the high-frequency current is supplied.

Specifically, the output power P0 with the lower power value which is not 0 watt is outputted as shown in FIGS. 24 and 25. In such a status, when the foot switch 4 is switched on and then the conductive perfusate is fully filled in the lesion portion, and the active electrode and the return electrode are normally held in the conductive solution, the high-frequency power is outputted so that the output value of the high-frequency power gradually increases. In a status in which the low current value is outputted, the foot switch 4 is switched on and then the conductive perfusate is fully filled in the lesion portion and the active electrode and the return electrode are normally held in the conductive solution, the high-frequency power is not outputted so that the output value of the high-frequency power gradually increases.

Therefore, the discharge operation in the incomplete status is prevented.

As mentioned above with reference to FIGS. 24 and 25, according to the third embodiment, the output power supplied to the treatment electrode gradually increases and the discharge operation is detected in the treatment electrode, thus the output power upon detecting the discharge operation or the preset output power lower than this is maintained. As compared with the conventional electric operation apparatus, since the discharge operation is performed with the lower power at the necessary and sufficient level, the unnecessary power is not needed. As a result, the costs reduce because the capacitance of the power supply decreases.

Upon increasing the output power, the start time of the discharge operation changes depending the temperature in conductive solution. Therefore, only the evaporation of the conductive solution around the treatment electrode takes a long time and needs the power which is not necessary. Then, the conductive solution supplied in the celom is heated.

Referring to FIG. 18, the heater 9 is arranged to the halfway of the sterilizing tube 8. The heater 9 heats the physiological saline from 36 to 40° C. as the body temperature. If the physiological saline is previously heated before the operation, the temperature of physiological saline reduces to the room temperature, e.g., 25° C. (degrees C.) in accordance with the passage of time. As compared with non-heated physiological saline, the heated physiological saline evaporates earlier around the treatment electrode. Thus, the power necessary for evaporation may be low.

Further, a hemostatic material is mixed in the physiological saline. Because the treated and resected anatomy is stanched upon treating the anatomy using the resectoscope.

With the above-mentioned structure, the electric operation apparatus is realized without the unnecessary power consumption. The means for heating the conductive solution is provided and therefore the treatment time of the treatment electrode is similar. Further, if the operator switches on the foot switch in the status in which the conductive solution as the perfusate is not filled in the lesion portion, the discharge operation is not performed in the incomplete status in the treatment electrode.

According to the third embodiment, the electric operation apparatus can be realized without the unnecessary power conduction.

(Fourth Embodiment)

Hereinbelow, a fourth embodiment will be described with reference to the drawings. The same reference numeral as the first embodiment denotes the same component.

Figure 27:
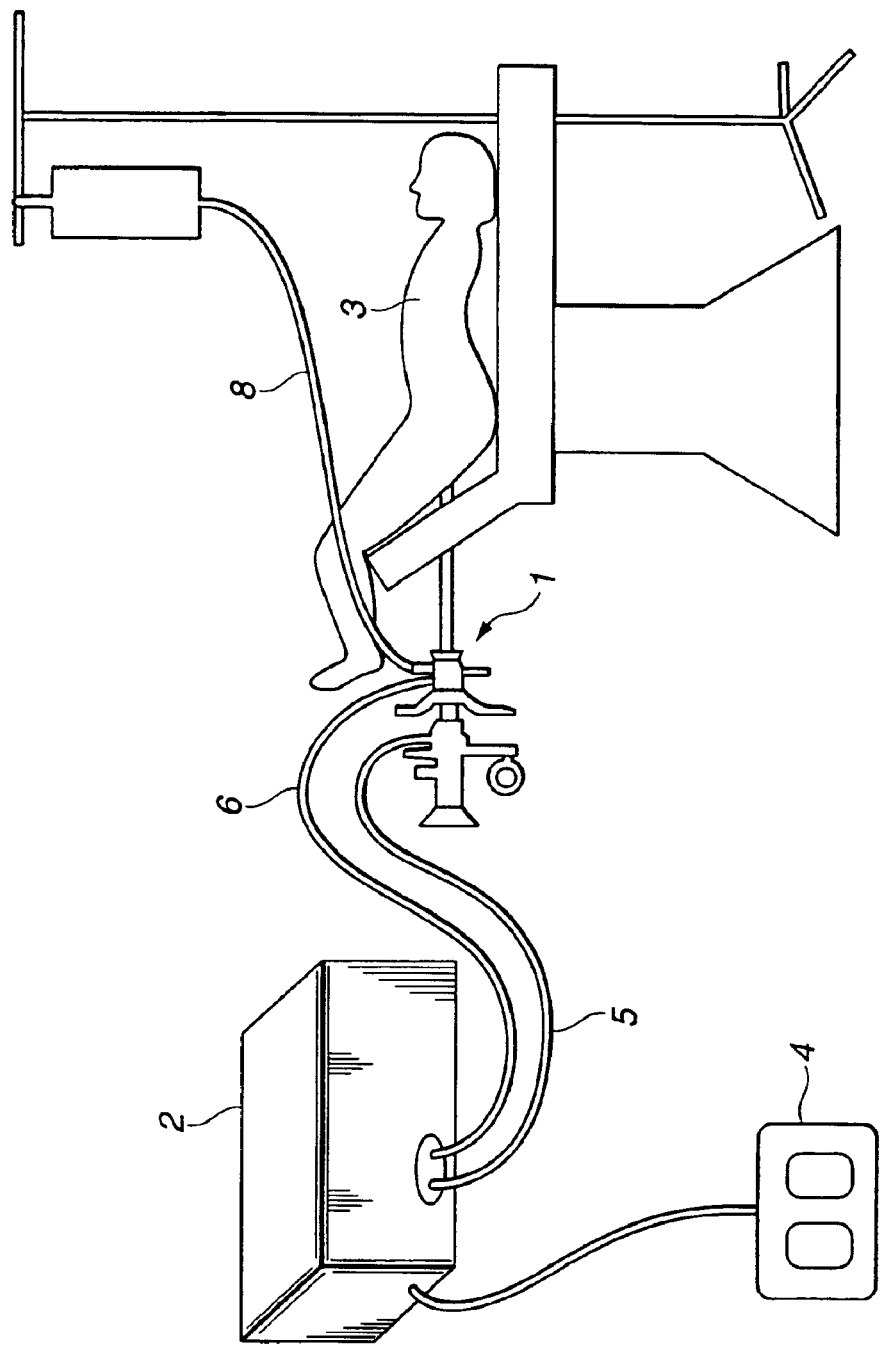
FIG. 27 is an explanatory diagram showing a status of electric operation using a resectoscope apparatus according to a fourth embodiment of the present invention.
Figure 28:
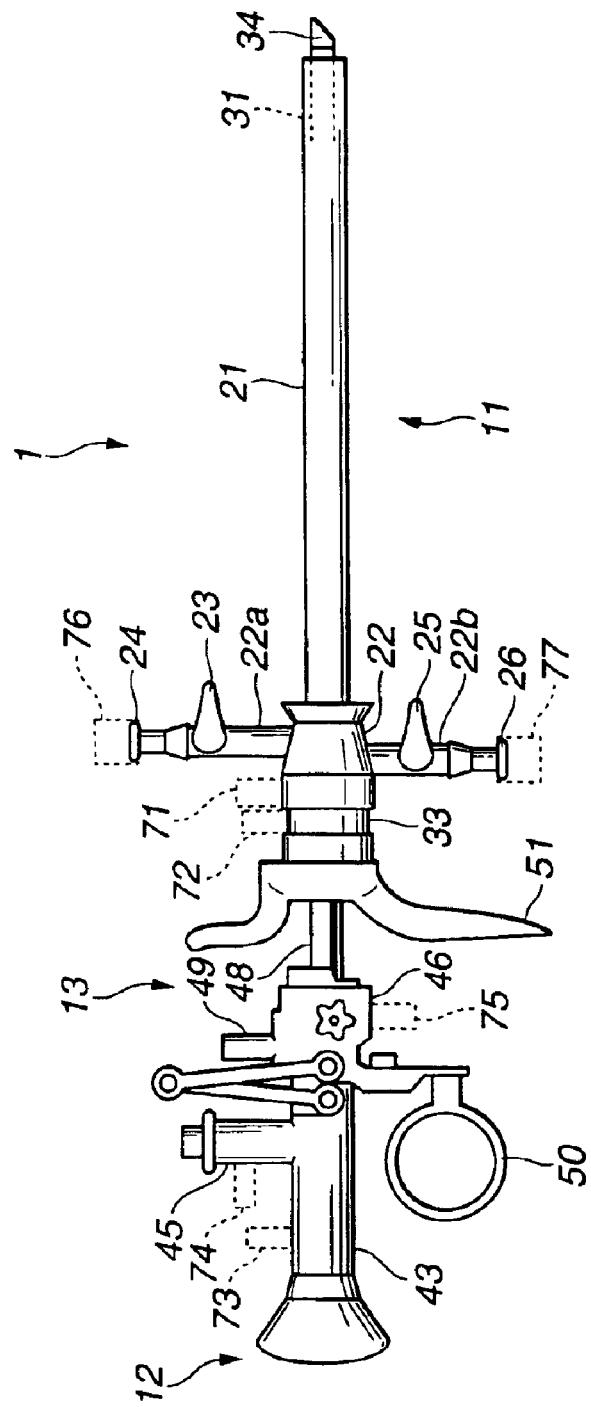
FIG. 28 is a side view showing the structure of a resectoscope according to the fourth embodiment.
Figure 29:
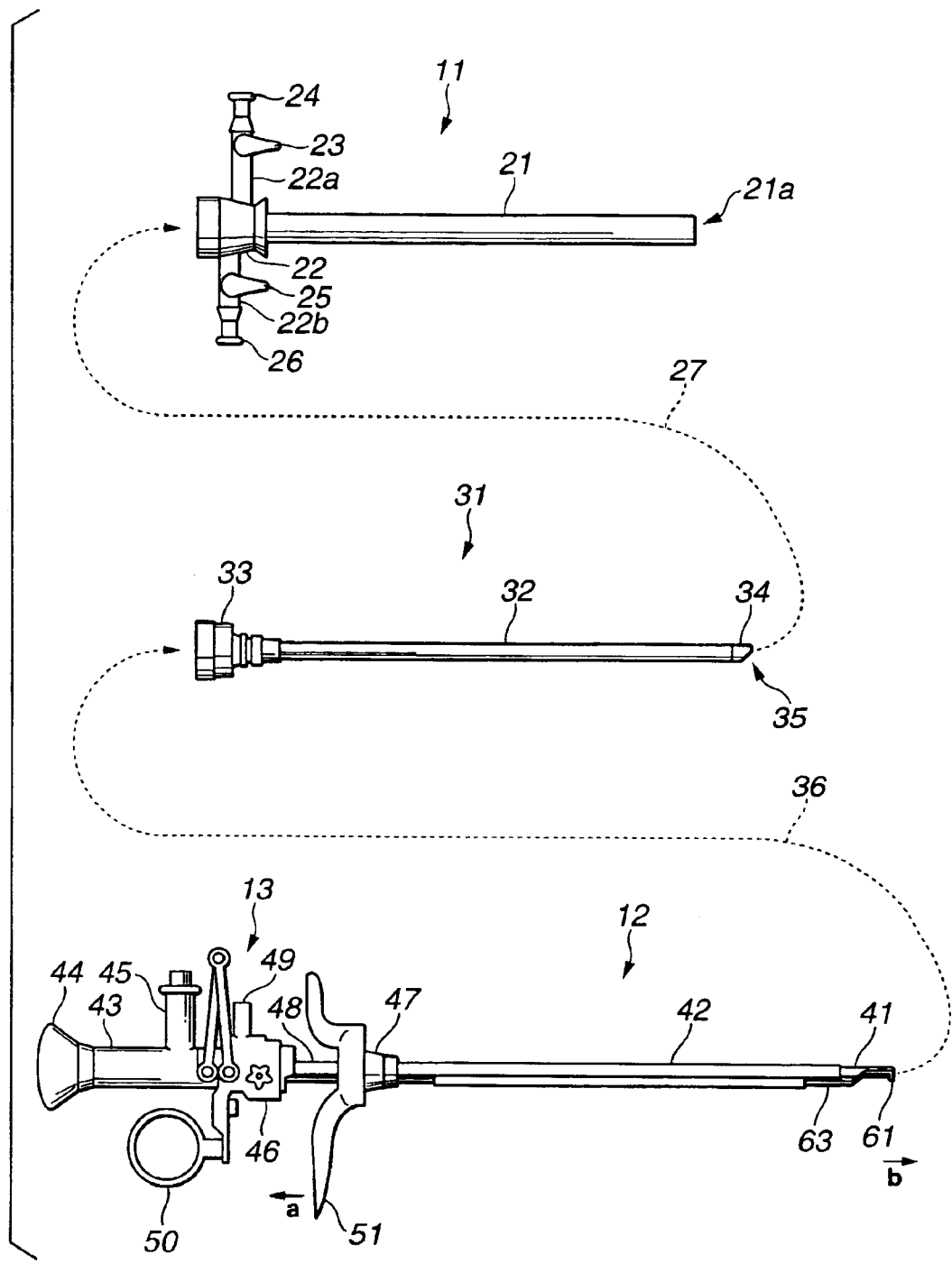
FIG. 29 is an assembly diagram for explaining the structure of the resectoscope according to the fourth embodiment.
Figure 30:
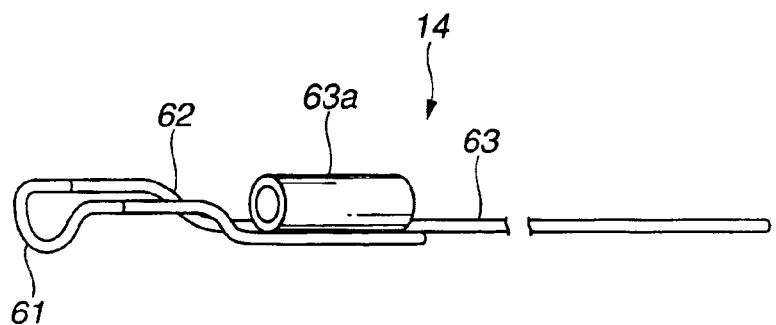
FIG. 30 is a perspective view showing the structure of an electrode unit according to the fourth embodiment.
Figure 32:
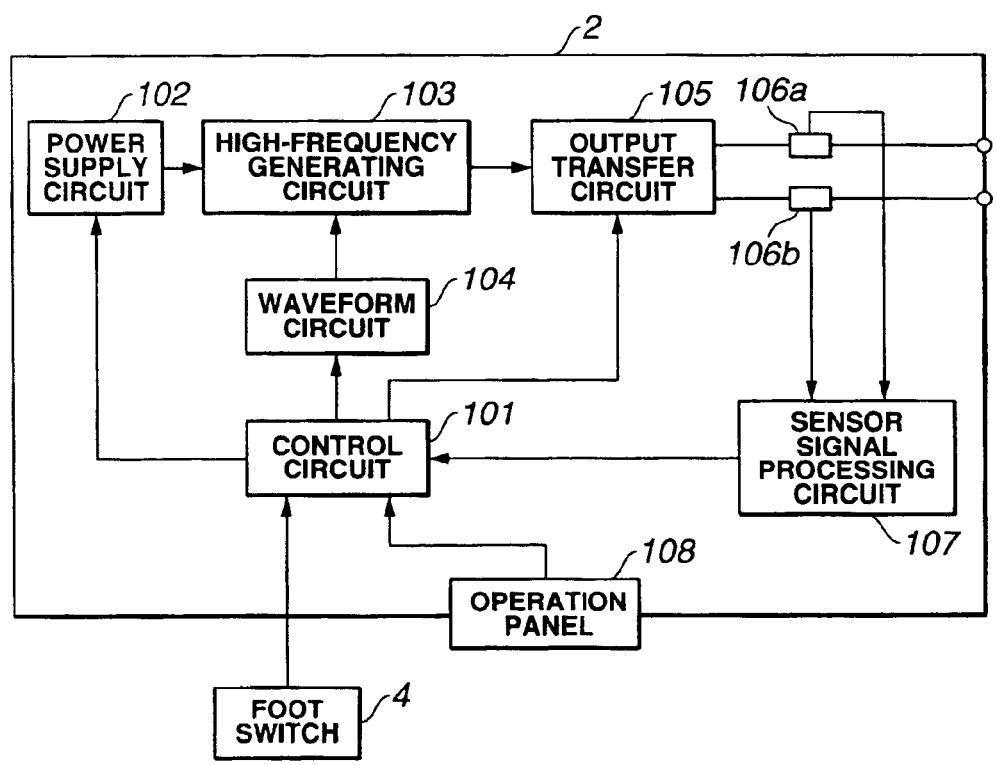
FIG. 32 is a block diagram showing the structure of a high-frequency power supply device according to the fourth embodiment.
Figure 31:
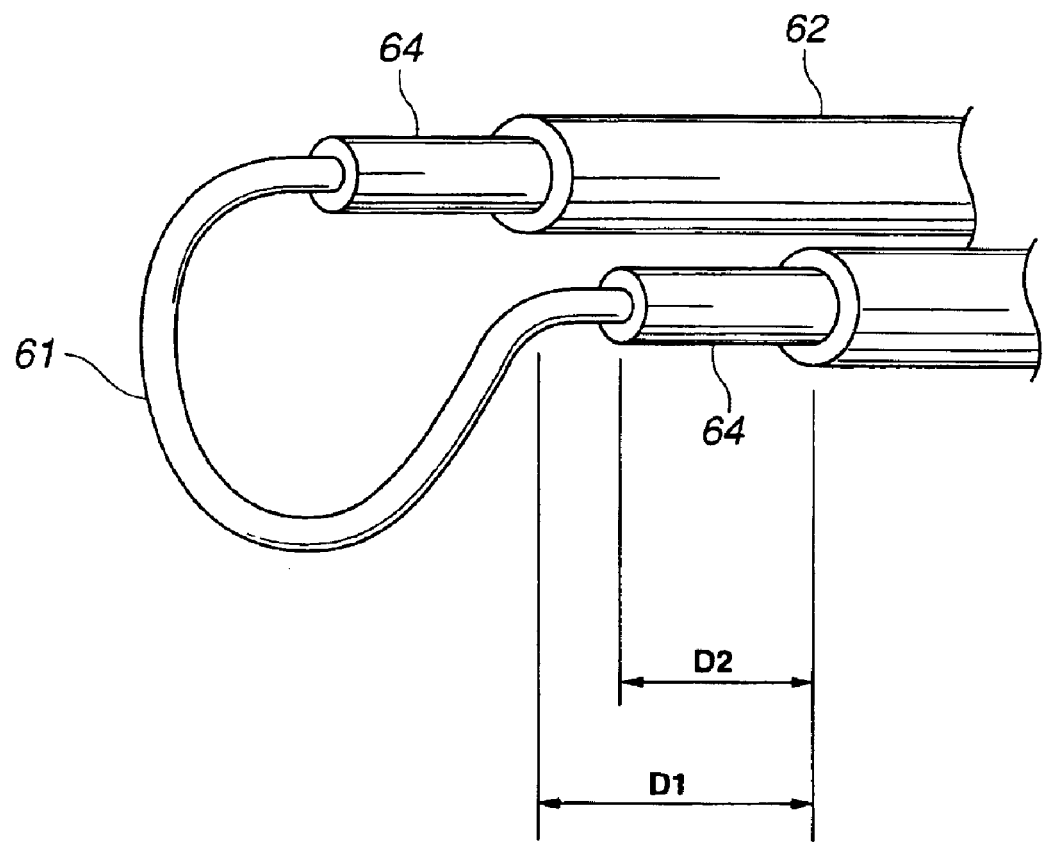
FIG. 31 is an enlarged perspective view showing a distal end portion of the electrode unit according to the fourth embodiment.
Figure 33:
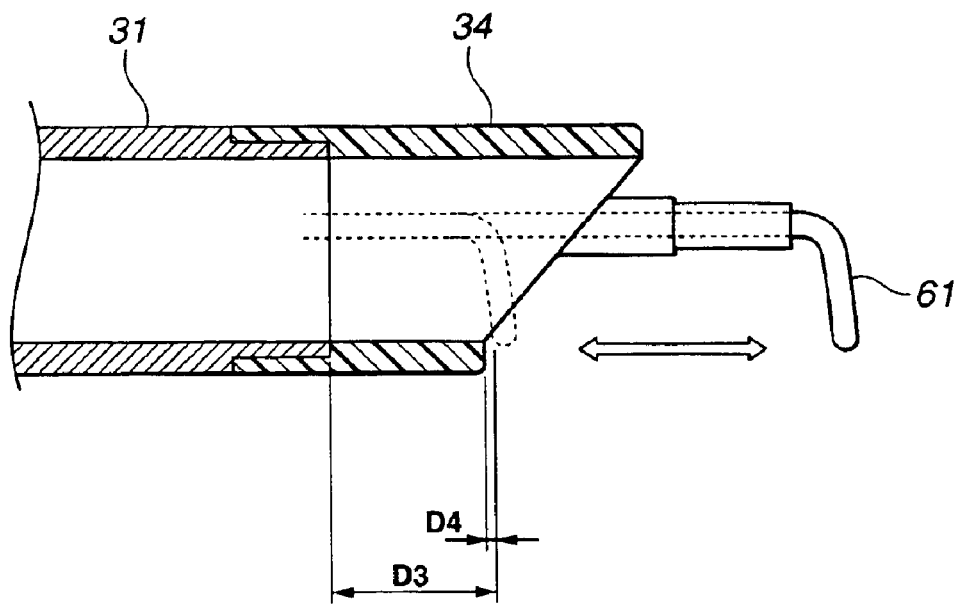
FIG. 33 is an explanatory diagram showing a positional relationship between a treatment electrode and a sheath distal end portion according to the fourth embodiment.
Figure 34:
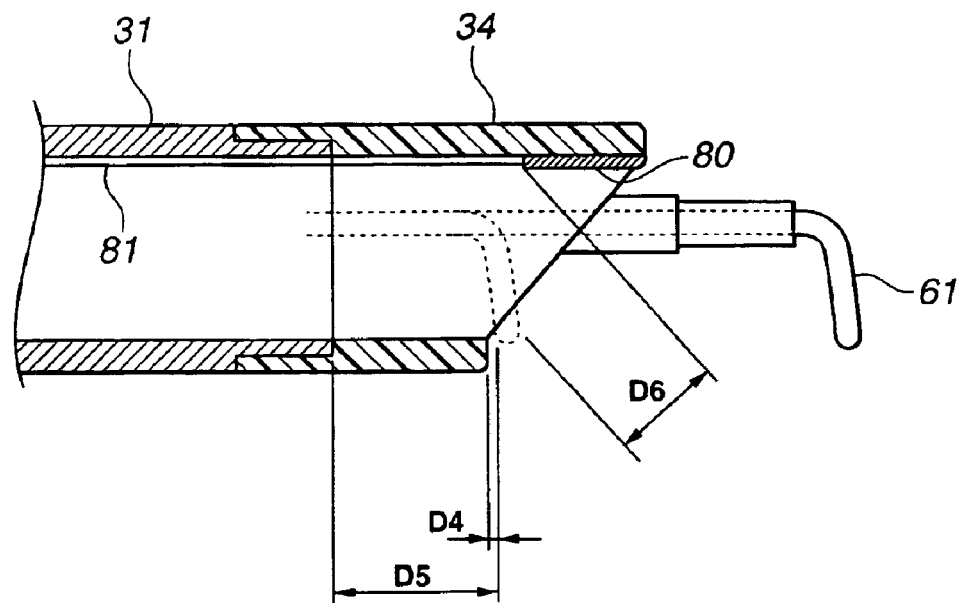
FIG. 34 is an explanatory diagram showing a positional relationship between the treatment electrode and the sheath distal end portion when the return electrode is arranged to a scope distal end portion according to the fourth embodiment.

FIGS. 27 to 34 are diagrams according to the fourth embodiment. FIG. 27 is an explanatory diagram showing a status of electric operation using a resectoscope apparatus. FIG. 28 is a side view showing the structure of the resectoscope. FIG. 29 is an assembly diagram for explaining the structure of the resectoscope. FIG. 30 is a perspective view showing the structure of an electrode unit. FIG. 31 is an enlarged perspective view showing a distal end portion of the electrode unit. FIG. 32 is a block diagram showing the structure of a high-frequency power supply device. FIG. 33 is an explanatory diagram showing a positional relationship between a treatment electrode and a sheath distal end portion. FIG. 34 is an explanatory diagram showing a positional relationship between the treatment electrode and the sheath distal end portion when the return electrode is arranged to a scope distal end portion.

FIG. 27 shows the status of electric operation using the resectoscope apparatus. Referring to FIG. 27, the transurethral resection is shown where the distal end portion of the resectoscope 1 is transurethrally inserted in the patient 3. The resectoscope apparatus mainly comprises the resectoscope 1 and the high-frequency power supply device 2 which supplies a high-frequency cautery current (hereinafter, referred to as active current) and which collects feedback current (hereinafter, referred to as return current), to/from a treatment electrode of an electrode unit.

The foot switch 4 connected to the high-frequency power supply device 2 is switched on or off to control the power supply to the treatment electrode from the high-frequency power supply device 2. The foot switch 4 is turned on and then the high-frequency current from the high-frequency power supply device 2 is supplied to the treatment electrode of the resectoscope 1 via the cable 5. As will be described later, the return current is collected via the cable 6.

Referring to FIG. 27, the physiological saline with conductivity as perfusate to the celom such as the bladder is supplied to the resectoscope 1 from the physiological saline pack 7 via the sterilizing tube 8. The operator fills the celom with the physiological saline, then inserts the resectoscope 1 to the celom, moves the treatment electrode to the surface of the anatomy for the incision and resection while viewing the endoscope image for observing the celom, and turns on the switch of the foot switch 4 for the incision.

Referring to FIG. 28, the resectoscope 1 comprises the hollow outer sheath 11 having the piercing hole as the mantle tube, the hollow inner sheath 31 having the piercing hole and inserted in the outer sheath 11, the scope 12 arranged in the piercing hole of the inner sheath 31, the handle portion 13 as an operating portion, and the electrode unit 14 (refer to FIG. 30) arranged together with the scope 12 in the piercing hole of the inner sheath 31.

The outer sheath 11 comprises the hollow inserting portion 21 which is inserted in the celom via the urethra, and the proximal main body portion 22 arranged to the rear end of the inserting portion 21. The proximal main body portion 22 has the two fluid tubes 22a and 22b at the side periphery thereof. Specifically, the fluid tube 22a comprises the cock 23 and the solution supply cap 24 which transmit the physiological saline or the like with the conductivity as the perfusate at the treatment portion. The fluid tube 22b comprises the cock 25 and the solution drain cap 26 which drain the physiological saline. The tube for transmitting the solution is connected to the solution supply cap 24. The tube for draining the solution is connected to the solution drain cap 26 forming the tube connecting means. The solution transmission and the solution drain are controlled by moving the cocks 23 and 25.

Referring to FIG. 29, the inner sheath 31 comprises the hollow inserting portion 32 which is inserted in the outer sheath 11, the proximal main body portion 33 which is arranged to the rear end of the inserting portion 32, and the distal end member 34 which is made of a hard non-conductive member such as a resin member. As shown by a dotted line 27 in FIG. 29, the inner sheath 31 is inserted from the opening portion of the proximal main body portion 22 on the rear side thereof and is arranged in the inserting portion 21. Incidentally, only the inner sheath 31 is attached and used, without using the outer sheath 11.

The scope 12 comprises the hard inserting tube 41 which is inserted and arranged into the elongated inner sheath 31 incorporating an observation optical system, the guide tube 42 to which the inserting tube 41 is inserted, and the proximal portion 43 which is arranged to the base end of the guide tube 42. The proximal portion 43 comprises the ocular portion 44 for operator's visually viewing operation at the base end of the proximal portion 43. Further, the proximal portion 43 comprises, at the side portion thereof, the light guide connecting portion 45 to which the light guide (not shown) for supplying illumination light for observation to the observing portion is connected. The scope 12 is inserted from the opening portion on the back of the proximal main body portion 33 together with the electrode unit 14 and is arranged in the inner sheath 31, as shown by a dotted line 36 in FIG. 29.

Referring to FIG. 30, the electrode unit 14 inserted and arranged in the inner sheath 31 mainly comprises the treatment electrode 61 arranged to the edge side and made of a hard metal member, the bifurcating arm member 62 having a parallel portion in the inserting axis of the scope 12, and the elongated metal pipe 63 which is extended from a proximal portion of the bifurcating arm portion 62 to the rear side thereof.

Specifically, referring to FIG. 31, the treatment electrode 61 is formed by loop-shaping an elongated, wire-shaped, and hard metal member, the conductive wiring integrally connected to both end portions of the loop-shaped electrode is covered with the insulating member 64 as a holding member for holding the electrode, the treatment electrode 61 is inserted in the bifurcating arm member 62 formed of a metal tube and passes through the metal pipe 63. The conductive wiring is connected to the electrode fixing unit (not shown) in the slider 46 which will be described later at the proximal portion of the metal pipe 63. Further, the treatment electrode 61 and the bifurcating arm member 62 are hook-shaped at the edge of the electrode unit 14 as the active electrode, and a predetermined angle is set between the plane including the loop-shaped treatment electrode 61 and the inserting axis of the scope 12.

Furthermore, the loop-shaped treatment electrode 61 is arranged far away from the distal end portion of the metal tube of the bifurcating arm member 62 by a prescribed distance D1 or more so as to certainly prevent the dielectric breakdown due to the discharge operation from the treatment electrode 61 to the metal-tube distal end portion of the bifurcating arm member 62. The insulating member 64 for holding both end portions of the treatment electrode 61 has a portion exposing from the metal-tube distal end portion of the bifurcating arm member 62 with a prescribed length D2 or more so as to prevent the deterioration due to the heat generated in the electrode unit.

The electrode unit 14 as the active electrode is arranged in the inner sheath 31 so that the treatment electrode 61 can advance and return in the inserting direction of the inner sheath 31 at the opening portion 35 of the distal end member 34 thereof. The proximal portion of the metal pipe 63 having the treatment electrode 61 and the bifurcating arm member 62 on the edge side thereof is inserted in the inserting portion 32 and the proximal main body portion 33 of the inner sheath 31, is extended from the base end surface of the proximal main body portion 33, and is fixed to the slider 46 which will be described later.

The handle portion 13 mainly comprises the sheath connecting portion 47 which is detachably connected to the proximal main body portion 33 of the inner sheath 31, the guide tube 48 which protrudes from the rear end surface of the sheath connecting portion 47 rearward and in which the inserting tube 41 of the scope 12 is inserted, and the substantially pipe-shaped slider 46 which is slidably held by the guide tube 48. The lever-shaped finger-hook portion 51 is integrally fixed to the sheath connecting portion 47. The slider 46 comprises the electrode fixing portion (not shown)

as the electrically connecting portion to the electrode connecting portion at the rear end portion of the. electrode unit 14, the connector 49 for high-frequency power supply to which the cable 5 for the power supply extended from the high-frequency power supply device 2 is detachably connected, and the thumb-hook ring 50 which is ring-shaped and to which the operator's thumb is hooked.

The slider 46 and the sheath connecting portion 47 are connected by an elastic member such as a spring (not shown) so that they are energized to be away from each other. That is, the slider 46 is always energized to the ocular portion 44 by the elastic member. The operator properly reduces the distance between the finger-hook portion 51 of the sheath connecting portion 47 and the thumb-hook ring 50 arranged to the slider 46 while gripping the finger-hook portion 51 and the thumb-hook ring 50, thereby moving the slider 46 in the direction of the edge of the scope 12 with respect to the guide tube 48. The treatment electrode 61 in the electrode unit 14 moves to be projected in the edge direction of the distal end member 34 of the inner sheath 31 from the opening portion 35.

When no manual force acts to the finger-hook portion 51 and the thumb-hook ring 50, a prescribed positional relationship is established between the treatment electrode 61 and the distal end portion of the inner sheath 31 in the inserting direction of the scope 12. That is, the base end side of the guide tube 48 is integrally fixed to the proximal portion 43 of the scope 12 so as to prevent the falling off from the guide tube 48 in the slider 46 and to regulate a lead-in position upon advancing and returning the treatment electrode 61. However, when the force acts to the finger-hook portion 51 and the thumb-hook ring 50 in a direction shown by an arrow a in FIG. 29 to reduce the distance, the inserting tube 41 does not move but the treatment electrode 61 moves in a direction shown by an arrow b in FIG. 29 so that it is projected in the edge direction of the scope 12.

The connector 49 for the high-frequency power supply arranged to the slider 46 is electrically connected to the electrode fixing unit by, e.g., a lead wiring. Thus, the cable 5 from the high-frequency power supply device 2 is connected to the connector 49 for the high-frequency power supply so that it is energized to the treatment electrode 61 in the electrode unit 14 for the treatment of the lesion portion. The resectoscope apparatus measures leak current by obtaining the difference between the current value supplied to the treatment electrode 61 and the current value of the return current.

Referring to FIG. 32, the high-frequency power supply device 2 comprises the control circuit 101 for receiving a signal from the foot switch 4 or the operating panel 108 and for controlling the power supply, the power supply circuit 102 for generating DC power under the control of the control circuit 101, the high-frequency generating circuit 103 for switching the DC current from the power supply circuit 102 and for generating high-frequency power, the waveform circuit 104 for supplying a waveform signal with the high-frequency current generated by the high-frequency generating circuit 103 under the control of the control circuit 101 to the high-frequency generating circuit 103, the output transfer circuit 105 for amplifying a high-frequency voltage with the high-frequency power generated by the high-frequency generating circuit 103, for applying the amplified voltage between the terminal for the treatment electrode 61 and the terminal for the return current, and for supplying the high-frequency current to the treatment current 61, the current sensors 106a and 106b for detecting the high-frequency current outputted from the output transfer circuit 105, and the sensor signal processing circuit 107 for A/D converting the current values detected by the current sensors 106a and 106b.

The control circuit 101 controls the power supply circuit 102 and the waveform circuit 104 based on digital current data from the sensor signal processing circuit 107, and controls the power upon resecting and coagulating the anatomy by using discharge current between the treatment electrode 61 and the anatomy. That is, the treatment electrode 61 comes into contact with the anatomy under the conductive solution and the high-frequency current is energized to the treatment electrode 61. Then, the high-frequency current flows between the treatment electrode 61 and the return electrode (which will be described later), and the treatment electrode 61 is heated. Bubbles are generated from the conductive solution on the outer peripheral surface of the treatment electrode 61. The bubbles cover the treatment electrode 61 and then resistance sharply increases between the treatment electrode 61 and return electrode, thus to enter the insulating status. In accordance therewith, the voltage rises and the discharge operation is caused between the treatment electrode 61 and the anatomy. The treatment is performed while the anatomy is resected and coagulated by the high-frequency current due to the discharging operation.

In the resectoscope 1, the inserting portion 21 of the outer sheath 11, the proximal main body portion 22, the fluid tube 22a, the solution supply cap 24, the fluid tube 22b, and the solution drain cap 26 are made of a conductive member such as metal. The inserting portion 32 and the proximal main body portion 33 of the inner sheath 31 are made of the conductive member such as the metal. Therefore, the outer sheath 11 is electrically conductive to the inner sheath 31. The guide tube 42, the sheath connecting portion 47, the guide tube 48, the slider 46, and the proximal portion 43 in the scope 12 are made of the conductive member such as the metal, and the guide tube 48 is electrically conductive to the outer sheath 11, the inner sheath 31, or the scope 12.

According to the fourth embodiment, the resectoscope apparatus has the conventional structure in which the return electrode is arranged to the distal end portion of the resectoscope 1 while the conductive solution such as the physiological saline filled in the celom intervenes. In addition, the outer sheath 11 or portions electrically conductive to the outer sheath 11, e.g., the following portions (1) to (5) can be used as the return electrode.

(1) Proximal portion of the outer sheath 11
(2) Proximal portion of the inner sheath 31
(3) Proximal portion of the scope 12 or the light guide connecting portion 45
(4) Handle portion 13
(5) Solution supply cap 24 and solution drain cap 26

In the case of setting the portions (1) to (5) as the return electrode, any of the connectors 71 to 77 is arranged at a position shown by a broken line in FIG. 28 so as to connect the cable 6 for the return current extended from the high-frequency power supply device 2 in the resectoscope 1. The current from the active electrode flows to the outer sheath 11 or the conductive member electrically conductive to the outer sheath 11 via the conductive solution, and the return current is collected via the connector. In the case of collecting the return current from the outer sheath 11 or the conductive member conductive to the outer sheath, the return current is collected via the conductive member due to the difference in impedance if the anatomy comes into contact with the outer sheath 11.

In this case, the lead-in position of the treatment electrode 61 by operating the handle portion 13 is regulated to have a positional relationship shown in FIG. 33. Thus, the discharge operation is prevented without fail between the treatment electrode 61 and the outer sheath 11 or the conductive member electrically conductive to the outer sheath 11.

In the resectoscope 1 according to the fourth embodiment, the distal end portion of the inner sheath 31 is projected to the side of the treatment electrode 61 from the outer sheath 11. A minimum distance D3 is prescribed between the treatment electrode 61 and the distal end portion of the inner sheath 31 upon the lead-in of the treatment electrode 61, and the distal end member 34 is arranged by a distance D4 shorter than the distance D3. Thus, the discharge operation is prevented without fail between the treatment electrode 61 and the inner sheath 31. The distance D4 is the minimum distance which bakes the anatomy by the discharge operation between the treatment electrode 61 and the anatomy and which enables the treatment electrode 61 to be led in and also enables the anatomy to be scrubbed and cut by the distal end member 34 to be detachable.

Referring to FIG. 34, the above relationship is the same as that of the case of additionally arranging a return electrode 80 at an upper surface in the distal end member 34 and connecting the return electrode 80 to a connector for the return current via a lead wiring 81. In other words, upon leading in the treatment electrode 61, a minimum distance D5 between the treatment electrode 61 and the distal end portion of the inner sheath 31 is regulated to prevent the discharge operation between the treatment electrode 61 and the inner sheath 31 without fail. Further, a distance D4 between the distal end member 34 and the treatment electrode 61 is set to be shorter than a distance D6 between the return electrode 80 and the treatment electrode 61. In this case, as compared with the example shown in FIG. 33 in which the return electrode is made of the outer sheath 11 or the conductive member electrically conductive to the outer sheath 11, a relationship of (D5≦D3) is established under the condition in which the passage of the return current from the return electrode 80 is insulated from the outer sheath 11 and the conductive member electrically conductive to the outer sheath 11.

In other words, the distances D3 and D5 correspond to the insulating distances for preventing the discharge operation between the treatment electrode 61 and the inner sheath 31 in the conductive solution, not with the intervention of the distal end member 34 as the non-conductive member but without the intervention of the distal end member 34. Referring to FIGS. 33 and 34, the insulating distances are schematically shown. This can be applied to the case of the distance D1 between the treatment electrode 61 and the metal-tube distal end portion of the bifurcating arm member 62.

Strictly, the leak current cannot completely be prevented between the treatment electrode 61 and the distal end portion of the inner sheath 31. However, the securing of the above-mentioned distances certainly prevents the current which causes the bubbles of the around-conductive solution and the formation of the discharge path. These insulating distances are obtained and set by simulation and experiment of the spatial distance and creepage distance for insulation necessary for the prevention of the discharge operation in consideration of necessary insulating intensity, the size of applied voltage and the size of the predicted over-voltage, the electric properties of the portions, various conditions such as the property of conductive solution and the temperature, and the dimension of the related portions.

In the case of independently providing the return electrode 80, the passage of the return current may be insulated from the outer sheath 11 and the conductive member electrically conductive to the outer sheath 11 by connecting the return electrode 80 to the connector for the return current via the lead wiring 81. However, any of the above-mentioned connectors 71 to 77 can be used by electrically connecting the independently provided return electrode 80 to any of the outer sheath 11 and the conductive member electrically conductive to the outer sheath 11.

In the electric operation using the resectoscope apparatus with the above structure, as mentioned above, the inserting portion 21 of the resectoscope 1 is inserted from the urethra and the opening portion 35 of the distal end member 34 is arranged near the lesion portion while observing the urethra via the ocular portion 44 of the scope 12 arranged in the inner sheath 31.

Next, after filling the celom with the physiological saline via the solution supply cap 24, the operator starts the energization to the treatment electrode 61. Then, the operator properly operates the handle portion 13 while observing the positional relationship between the lesion portion and the treatment electrode 61 via the ocular portion 44, he presses the treatment electrode 61 to the anatomy near the lesion portion, and he properly operates the thumb-hook ring 50 so that it moves to the hand portion side. Consequently, the discharge operation between the treatment electrode 61 and the anatomy bakes the anatomy of the lesion portion, the treatment electrode 61 is led in, and the anatomy is scrubbed and detached by the distal end member 34, thus to enabling the resection.

In this case, as mentioned above, the treatment electrode 61 forming the electrode unit 14 is arranged at the position projected from the distal end portion of the metal tube of the bifurcating arm member 62 by the prescribed distance D1 or more. Further, the insulating member 64 for holding both end portions of the treatment electrode 61 has the portion exposing from the metal-tube distal end portion of the bifurcating arm member 62 with the prescribed length D2 or more. As a consequence, it is possible to certainly prevent the dielectric breakdown due to the discharge operation from the treatment electrode 61 to the metal-tube distal end portion of the bifurcating arm member 62. Further, the deterioration in insulating member 64 is prevented and the baking performance is assured.

When the treatment electrode 61 is led in and it is most contact to the conductive member of the edge of the resectoscope, neither the discharge operation nor the short-circuit is caused between the treatment electrode 61 and the outer sheath 11 and the conductive member electrically conductive to the outer sheath 11 and the baking performance of the treatment electrode 61 is ensured. In addition, the current is effectively collected to the return electrode from the treatment electrode 61 contact to the treatment portion and the treatment is certainly performed. This results in the smooth and effective treatment irrespective of the expansion of the narrow celom by filling it with the conductive solution. The burden to the operator, the related operators, and the patient is exceedingly reduced.

As mentioned above, according to the fourth embodiment, the baking performance of the active electrode is assured by certainly preventing the adverse discharge operation and short circuit between the conductive member forming the resectoscope and the active electrode for transmitting the high-frequency current to the anatomy. Further, the product quality is improved by preventing the deterioration in portions of the resectoscope due to the adverse discharge operation and short circuit.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A resectoscope apparatus comprising:
   a high-frequency power generating unit which generates high-frequency power for treating the anatomy;
   a first electrode which supplies to the anatomy, the high-frequency power generated by the high-frequency power generating unit;
   a solution supply unit which supplies a conductive solution around the electrode; and
   a second electrode which is arranged in the conductive solution supplied by the solution supply unit and which returns the high-frequency power supplied to the anatomy from the first electrode,
   wherein the first electrode has two parallel lead members, and a treatment electrode connected to an edge of the parallel lead members, and
   when a first segment is in parallel with the plane on which the parallel lead members exist and has the maximum width of the treatment electrode and a second segment is vertical to the first segment and has the maximum distance between an intersection to the first segment and an intersection to the treatment electrode, a length a of the first segment and a length b of the second segment satisfy a relationship of (a>2·b).

2. A resectoscope apparatus according to claim 1, wherein the diameter of the treatment electrode is maximum at an intersection between the second segment and the treatment electrode.

3. An electric operation apparatus comprising:
   a high-frequency generating unit which generates high-frequency current;
   a high-frequency generation instructing unit which instructs the generation of the high frequency to the high-frequency generating unit;
   an active electrode which transmits the high-frequency current to the anatomy;
   a return current collecting unit which collects the high-frequency current which flows to the anatomy from the active electrode; and
   a control limit which controls output power of the high-frequency current transmitted to the anatomy from the active electrode,
   wherein the control unit controls the output power so that it gradually increases after receiving the instruction for generating the high-frequency from the high-frequency generation instructing unit.

4. An electric operation apparatus according to claim 3, wherein the control unit controls the output power so that it maintains a constant value when the output power gradually increases and then is under a predetermined condition.

5. An electric operation apparatus according to claim 3, wherein the control unit controls the output power so that it reduces to and maintains a constant value which is a value lower than a value of the output power under a predetermined condition, when the output power gradually increases and then is under the predetermined condition.

6. An electric operation apparatus according to claim 3, further comprising:
   a heating unit which heats a conductive solution in the celom in which the active electrode comes into contact with the return current collecting unit.

7. An electric operation apparatus according to claim 3, further comprising:
   a solution evaporation determining means for determining an evaporation of the conductive solution,
   wherein the control unit determines based on the detected result of the solution evaporation detecting unit, whether or not it is under the predetermined condition.

8. An electric operation apparatus according to claim 7, wherein the solution evaporation determining means determines an impedance between the active electrode and the return current collecting unit, and the control unit determines whether or not it is under the predetermined condition depending on whether or not the impedance is a predetermined value or less.

9. An electric operation apparatus according to claim 3, further comprising:
   a conductive solution detecting unit which detects whether or not the conductive solution exists between the active electrode and the return current collecting unit,
   wherein when the conductive solution detecting unit detects that the conductive solution exists between the active electrode and the return current collecting unit, the control unit starts to increase the output power.

10. An electric operation apparatus according to claim 9, wherein in the conductive solution detecting unit, the conductive solution exists between the active electrode and the return current collecting unit based on an impedance between the active electrode and the return current collecting unit.

11. An electric operation apparatus comprising:
    a high-frequency generating unit which generates high-frequency current;
    a high-frequency generation instructing unit which instructs the generation of the high frequency to the high-frequency generating unit;
    a resectoscope having an active electrode for transmitting the high-frequency current to the anatomy, and
    a control unit which controls output power of the high-frequency current transmitted to the anatomy from the active electrode,
    wherein the resectoscope has a connecting portion to the high-frequency generating unit so as to use at least one of a sheath and a scope of the resectoscope as a return current collecting unit, and
    the control unit receives the instruction for generating the high-frequency from the high-frequency generation instructing unit and then controls the output power so that it gradually increases.

12. An electric operation apparatus according to claim 11, wherein the control unit controls the output power so that it maintains a constant value when the output power gradually increases and then is under a predetermined condition.

13. An electric operation apparatus according to claim 11, wherein the control unit controls the output power so that it reduces to and maintains a constant value which is a value lower than a value of the output power under a predetermined condition, when the output power gradually increases and then is under the predetermined condition.

14. An electric operation apparatus according to claim 11, further comprising:
    a heating unit which heats a conductive solution in the celom in which the active electrode comes into contact with the return current collecting unit.

15. An electric operation apparatus according to claim 11, further comprising:

a solution evaporation determining means for determining an evaporation of the conductive solution, wherein the control unit determines based on the detected result of the solution evaporation detecting unit whether or not it is under the predetermined condition.

16. An electric operation apparatus according to claim 15, the solution evaporation determining means determines an impedance between the active electrode and the return current collecting unit, and the control unit determines whether or not it is under the predetermined condition depending on whether or not the impedance is a predetermined value or less.

17. An electric operation apparatus according to claim 11, further comprising:

a conductive solution detecting unit which detects whether or not the conductive solution exists between the active electrode and the return current collecting unit, wherein when the conductive solution detecting unit detects that the conductive solution exists between the active electrode and the return current collecting unit, the control unit starts to increase the output power.

18. An electric operation apparatus according to claim 17, wherein in the conductive solution detecting unit, the conductive solution exists between the active electrode and the return current collecting unit based on the impedance between the active electrode and the return current collecting unit.

19. A resectoscope apparatus comprising:

a high-frequency generating unit which generates high-frequency current;

a hollow sheath having conductivity which is inserted in the celom filled with a conductive solution;

an active electrode which transmits the high-frequency current to the anatomy; and a return electrode which is arranged to come into contact with the conductive solution and which collects current from the active electrode, wherein the active electrode is arranged to advance and return within a distance for preventing the discharge operation in the sheath or a conductive member that is electrically conductive to the sheath, and a non-conductive member is arranged so that a distance to the active electrode is shorter than a distance between the return electrode and the active electrode.

20. A resectoscope apparatus according to claim 19, wherein the return electrode is formed by the sheath or a conductive member electrically conductive to the sheath, and the non-conductive member is attached to an edge of the sheath.

21. A resectoscope apparatus according to claim 19, wherein the non-conductive member is attached to an edge of the sheath, and the return electrode is arranged to the non-conductive member.

22. A resectoscope apparatus according to claim 19, wherein the non-conductive member is a holding member for holding the active electrode.

* * * * *